(12) United States Patent
Pappalardo et al.

(10) Patent No.: US 9,962,448 B2
(45) Date of Patent: May 8, 2018

(54) COMPOUNDS AND METHODS FOR TARGETED IMMUNE SYSTEM DELIVERY

(71) Applicant: Northeastern University, Boston, MA (US)

(72) Inventors: Juan Sebastian Pappalardo, Escobar (AR); Micaela Toniutti, Udine (IT); Stefano Salmaso, Abano Terme (IT); Tatyana S. Levchenko, Revere, MA (US); Vladimir Torchilin, Charlestown, MA (US)

(73) Assignees: Northeastern University, Boston, MA (US); National Institute of Agricultural Technology, Ciudad Autonoma de Buenos Aires (AR); University of Padova, Padua (IT)

( * ) Notice: Subject to any disclaimer, the term of this patent is extended or adjusted under 35 U.S.C. 154(b) by 34 days.

(21) Appl. No.: 14/431,685

(22) PCT Filed: Oct. 4, 2013

(86) PCT No.: PCT/US2013/063567
§ 371 (c)(1),
(2) Date: Mar. 26, 2015

(87) PCT Pub. No.: WO2014/055941
PCT Pub. Date: Apr. 10, 2014

(65) Prior Publication Data
US 2015/0238621 A1    Aug. 27, 2015

Related U.S. Application Data

(60) Provisional application No. 61/709,616, filed on Oct. 4, 2012.

(51) Int. Cl.
| | | |
|---|---|---|
| *C07H 15/02* | (2006.01) | |
| *C07H 15/20* | (2006.01) | |
| *A61K 47/48* | (2006.01) | |
| *A61K 38/00* | (2006.01) | |
| *A61K 31/74* | (2006.01) | |
| *A61K 31/77* | (2006.01) | |
| *A61K 9/127* | (2006.01) | |
| *A61K 39/00* | (2006.01) | |
| *A61K 39/002* | (2006.01) | |
| *A61K 39/12* | (2006.01) | |
| *A61K 47/54* | (2017.01) | |
| *A61K 47/69* | (2017.01) | |

(52) U.S. Cl.
CPC ........ *A61K 47/48092* (2013.01); *A61K 9/127* (2013.01); *A61K 31/74* (2013.01); *A61K 31/77* (2013.01); *A61K 38/00* (2013.01); *A61K 39/002* (2013.01); *A61K 39/0005* (2013.01); *A61K 39/12* (2013.01); *A61K 47/549* (2017.08); *A61K 47/6911* (2017.08); *C07H 15/02* (2013.01); *C07H 15/20* (2013.01)

(58) Field of Classification Search
None
See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,675,189 A | 6/1987 | Kent et al. |
| 5,133,974 A | 7/1992 | Paradissis et al. |
| 5,407,686 A | 4/1995 | Patel et al. |
| 5,736,152 A | 4/1998 | Dunn |
| 6,436,914 B1 | 8/2002 | Sher et al. |
| 7,534,769 B2 | 5/2009 | Engler et al. |
| 2012/0202890 A1 | 8/2012 | Wu |

FOREIGN PATENT DOCUMENTS

WO    WO-2009/069966 A2    6/2009

OTHER PUBLICATIONS

Berge, S. M. et al., "Pharmaceutical Salts," Journal of Pharmaceutical Sciences, vol. 66, No. 1, pp. 1-19 (Jan. 1977).
Calarese, D. A. et al., "Dissection of the carbohydrate specificity of the broadly neutralizing anti-HIV-1 antibody 2G12," Proc. Natl. Acad. Sci. USA, vol. 102, No. 38, pp. 13372-13377 (Sep. 20, 2005).
Feinberg, H. et al., "Multiple modes of binding enhance the affinity of DC-SIGN for high mannose N-linked glycans found on viral glycoproteins," J. Biol. Chem., vol. 282, No. 6, pp. 4202-4209, 18 pages (Feb. 9, 2007).
Guo, Y. et al., "Structural basis for distinct ligand-binding and targeting properties of the receptors DC-SIGN and DC-SIGNR," Nat. Struct. Mol. Biol., vol. 11, No. 7, pp. 591-598 (Jul. 2004).
Hakkarainen, B. et al., "NMR study of hydroxy protons of di- and trimannosides, substructures of Man-9," Magn. Reson. Chem., vol. 45, No. 12, pp. 1076-1080 (Dec. 2007).
Hong, P. W. et al., "Human immunodeficiency virus envelope (gp120) binding to DC-SIGN and primary dendritic cells is carbohydrate dependent but does not involve 2G12 or cyanovirin binding sites: implications for structural analyses of gp120-DC-SIGN binding," J. Virol., vol. 76, No. 24, pp. 12855-12865 (Dec. 2002).
International Search Report and Written Opinion issued by the U.S. Patent and Trademark Office as International Searching Authority International Application No. PCT/US2013/063567 dated May 7, 2014 (10 pages).
Irvine, A. S. et al., "Efficient nonviral transfection of dendritic cells and their use for in vivo immunization," Nature Biotechnology, vol. 18, No. 12, pp. 1273-1278 (2000).

(Continued)

*Primary Examiner* — Traviss C McIntosh, III
(74) *Attorney, Agent, or Firm* — Posternak Blankstein & Lund LLP

(57) ABSTRACT

Compounds and methods for targeted immune system delivery are disclosed. Pharmaceutical compositions including the disclosed compounds and a pharmaceutically acceptable excipient are also disclosed. Methods of targeted delivery to an antigen-presenting cell, and methods of treating or preventing a disease or condition susceptible to treatment by immunomodulation are disclosed.

25 Claims, 11 Drawing Sheets

(56) References Cited

OTHER PUBLICATIONS

Jahnisch, H. et al., "Dendritic cell-based immunotherapy for prostate cancer," Clin. Dev. Immunol., vol. 2010, 8 pages (2010).
Kapsenberg, M. L., "Dendritic-cell control of pathogen-driven T-cell polarization," Nat. Rev. Immunol., vol. 3, No. 12, pp. 984-993 (Dec. 2003).
Kobayashi, K. et al., "Synthesis and Functions of Polystyrene Derivatives Having Pendant Oligosaccharides," Polymer Journal, vol. 17, No. 4, pp. 567-575 (1985).
Landi, A. et al., "High transfection efficiency, gene expression, and viability of monocyte-derived human dendritic cells after nonviral gene transfer," Journal of Leukocycte Biology, vol. 82, No. 4, pp. 849-860 (Oct. 2007).
Langer, R., "New methods of drug delivery," Science, vol. 249, No. 4976, pp. 1527-1533 (Sep. 28, 1990).
Marshak-Rothstein, A., "Toll-like receptors in systemic autoimmune disease," Nat. Rev. Immunol., vol. 6, No. 11, pp. 823-835 (Nov. 2006).
Medzhitov, R., Toll-like receptors and innate immunity, Nat. Rev. Immunol., vol. 1, No. 2, pp. 135-145 (Nov. 2001).
Meschi, J. et al., "Surfactant protein D binds to human immunodeficiency virus (HIV) envelope protein gp120 and inhibits HIV replication," J. Gen. Virol., vol. 86, Part 11, pp. 3097-3107 (Nov. 2005).
Modlin, R. L., "Immunology. A Toll for DNA vaccines," Nature, vol. 408, No. 6813, pp. 659-660 (Dec. 7, 2000).
Pappalardo, J. S. et al., "Improved transfection of spleen-derived antigen-presenting cells in culture using TATp-liposomes," J. Control Release, vol. 134, No. 1, pp. 41-46 (Feb. 20, 2009).
Riedl, P. et al., "Peptides containing antigenic and cationic domains have enhanced, multivalent immunogenicity when bound to DNA vaccines," J. Mol. Med., vol. 82, pp. 144-152 (2004).
Sandor, F. and Buc, M., "Toll-like receptors. I. Structure, function and their ligands," Folia Biol. (Praha), vol. 51, No. 5, pp. 148-157 (2005).
Sandor, F. and Buc, M. "Toll-like receptors. II. Distribution and pathways involved in TLR signaling", Folia Biol. (Praha), vol. 51, No. 6, pp. 188-197 (2005).
Sandor, F. and Buc, M., "Toll-like receptors. III. Biological significance and impact for human medicine," Folia Biol. (Praha), vol. 51, No. 6, pp. 198-203 (2005).
Schirmbeck, R. et al., "Antigenic Epitopes Fused to Cationic Peptide Bound to Oligonucleotides Facilitate Toll-Like Receptor 9-Dependent, but CD4+ T Cell Help-Independent, Priming of CD8+ T Cells," The Journal of Immunology, vol. 171, No. 10, pp. 5198-5207 (Nov. 15, 2003).
Tan, P. H. et al., "Creation of tolergenic human dendritic cells via intracellular CTLA4: a novel strategy with potential in clinical immunosuppression," Blood, vol. 106, No. 9, pp. 2936-2943 (Nov. 1, 2005).
Tan, P. H. et al., "Immunolipoplexes: An Efficient, Nonviral Alternative for Transfection of Human Dendritic Cells with Potential for Clinical Vaccination," Molecular Therapy, vol. 11, No. 5, pp. 790-800 (May 2005).
Tan, P. H. et al., "Modulation of human dendritic-cell function following transduction with viral vectors: implications for gene therapy," Blood, vol. 105, No. 10, pp. 3824-3832 (May 15, 2005).
Williams, R. L. and Urbe, S., "The emerging shape of the ESCRT machinery," Nat. Rev. Mol. Cell Biol., vol. 8, No. 5, pp. 355-368 (May 2007).
Yewdell, J. W. et al., "Making sense of mass destruction: quantitating MHC class I antigen presentation," Nat. Rev. Immunol., vol. 3, No. 12, pp. 952-961 (Dec. 2003).
Yoshikawa, T. et al., "Non-methylated CpG motif packaged into fusogenic liposomes enhance antigen-specific immunity in mice," Biol. Pharm. Bull., vol. 29, No. 1, pp. 105-109 (Jan. 2006).

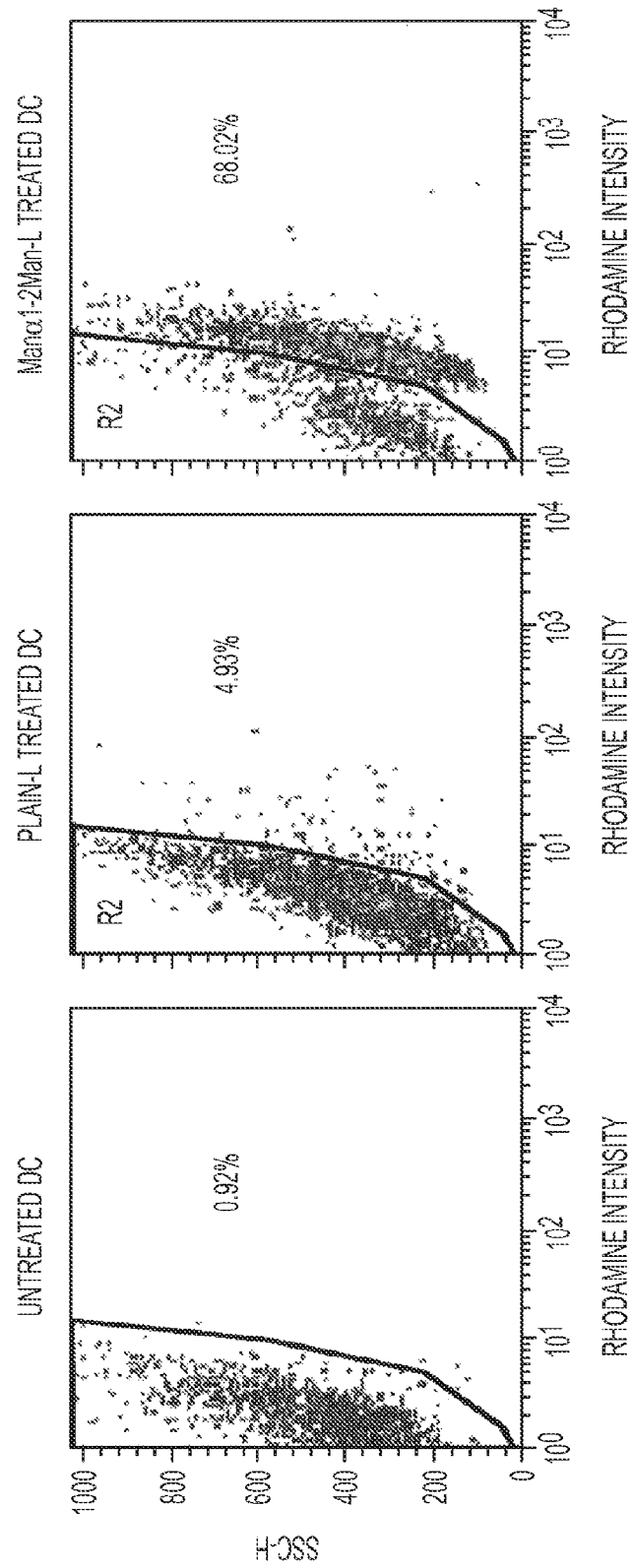

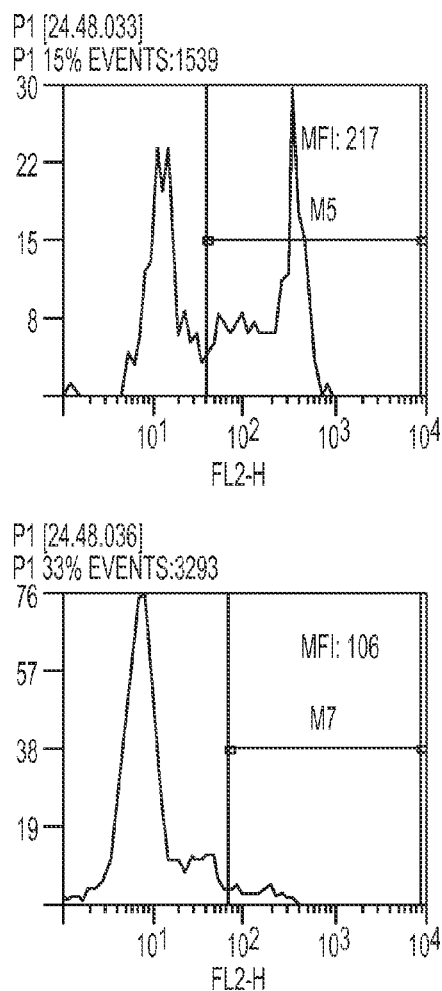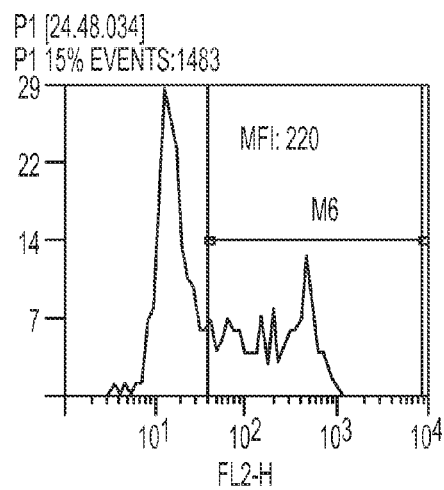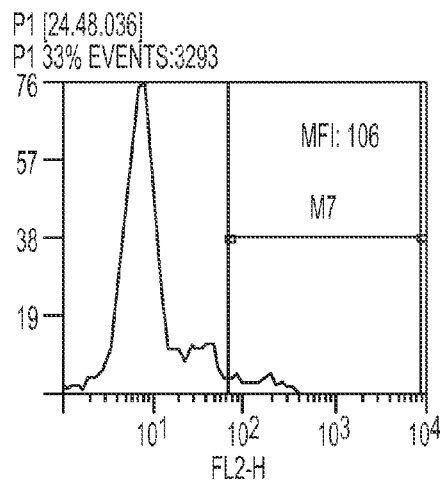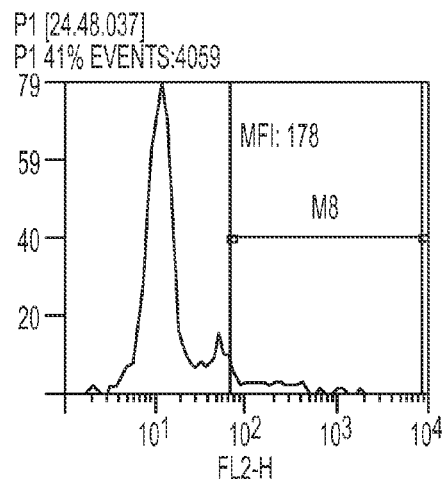
FIG. 5
CONTINUED

COMPOUNDS AND METHODS FOR TARGETED IMMUNE SYSTEM DELIVERY

CROSS-REFERENCE TO RELATED APPLICATIONS

This application is a national stage application of International Application No. PCT/US13/63567 entitled "Compounds and Methods for Targeted Immune System Delivery," filed on Oct. 4, 2013, which claims the benefit of priority of U.S. Provisional Application No. 61/709,616, filed on Oct. 4, 2012, the disclosures of each of which are hereby incorporated by reference in their entirety.

FIELD OF THE INVENTION BACKGROUND

The present invention relates generally to the field of immunology and, specifically, immune cell targeting and immune response modulation.

BACKGROUND

The immune system (IS) is a complex network of interacting cells, biological structures, and processes within an organism that protects against pathogens and foreign substances, destroys infected and malignant cells, and removes cellular debris. The IS maintains a delicate equilibrium between its cells. Some of the most important cells of the IS are the Blymphocytes (BL), macrophages (MØ), and dendritic cells (DC), which are called antigen-presenting cells (APCs). APCs are the key linkers between the innate and adaptive immune response. They play a crucial role that will lead to either an immune response or anergy towards an antigen. Dendritic cells are known as the most important APCs, as they are the only known cells able to prime naïve T lymphocytes (TL); APCs trigger and direct the immune response.

SUMMARY OF THE INVENTION

In some aspects, the instant application is directed to novel compounds, pharmaceutical formulations, and methods for targeted immune system delivery to antigen-presenting cells using the disclosed compounds.

In one aspect, a compound having the structure of Formula (I),

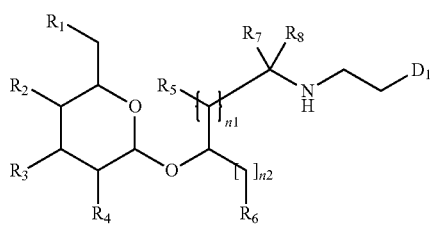

(I)

or a pharmaceutically acceptable salt or hydrate thereof is described, wherein $R_1$, $R_2$, $R_3$, $R_4$, $R_5$, and $R_6$ are each independently H, OH, O-monosaccharide, NHAc, or Me;

$n_1$ and $n_2$ are each independently 0, 1, 2, 3, or 4, provided that the sum of $n_1$ and $n_2$ is 4;

$R_7$ and $R_8$ are each independently hydrogen, or $R_7$ and $R_8$ together form an oxo (=O); and $D_1$ is a polymer selected from a group consisting of negative polymer, positive polymer, neutral polymer, linear or branched polymer, a lipid, hydrophobic carbon chain, nanoparticle organic molecule, nanoparticle inorganic molecule, drug, ribonucleic acids, peptide-nucleic acids (PNAs), a mixture thereof, and a derivative thereof.

In some embodiments, $D_1$ is a peptide or a protein.

In some embodiments, $D_1$ is a polymer including a derivative of nylon, PVC, silicone, latex, polyvinyl butyral, polyacrylonitrile, polystyrene, polyethylene, polyethyleneglycol (PEG), polyethyleneoxide (PEO), polyethyleneimine (PEI), polyoxymethylene (POM), biodegradable polymers such as polylactic acid (PLA), polylactic-co-glycolic acid (PLGA), etc., a mixture thereof, or a derivative thereof.

In some embodiments, $D_1$ is a PEG derivative selected from the group consisting of PEG (poly(ethylene glycol)), PEG-DSPE, PEGCer (PEG-ceramide), PEGCerC14 (PEGCer containing a 14-carbon fatty acyl chain), PEGCer-Czo (PEGCer containing a 20-carbon fatty acyl chain), PEG-COOH (carboxylated PEG-derivative), PEG-PE (poly(ethylene glycol)phosphatidylethanolamine), and PEG-Osu (poly(ethyelene glycol)hydroxysuccinimide ester).

In some embodiments, the PEG derivative includes PEG-DSPE, PEG-DPPE, PEG-DOPE, PEG-DMPE, PEG-ceramide, fluorescent PEG-DSPE derivative, Succinyl-PEG, Carboxylic Acid-PEG, Maleimide-PEG, PDP-PEG, Amine-PEG, Biotin-PEG, Cyanur-PEG, Folate-PEG, a mixture thereof, or a derivative thereof.

In some embodiments, the PEG-ceramide includes octanoyl-sphingosine, palmitoyl-sphingosine, or a mixture thereof.

In some embodiments, the fluorescent PEG-DSPE derivative is carboxyfluorescein-PEG-DSPE, rhodamine-PEG-DSPE, and derivatives thereof.

In some embodiments, the compound has the following structures:

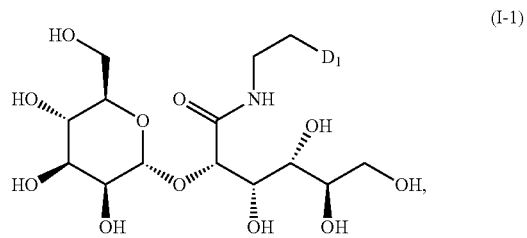

(I-1)

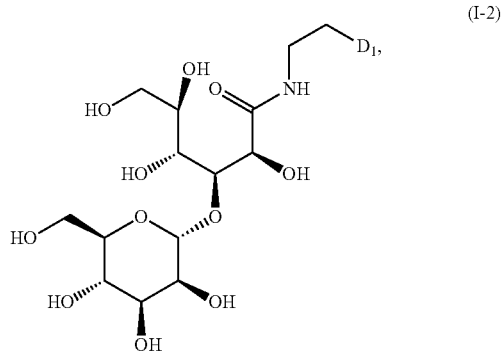

(I-2)

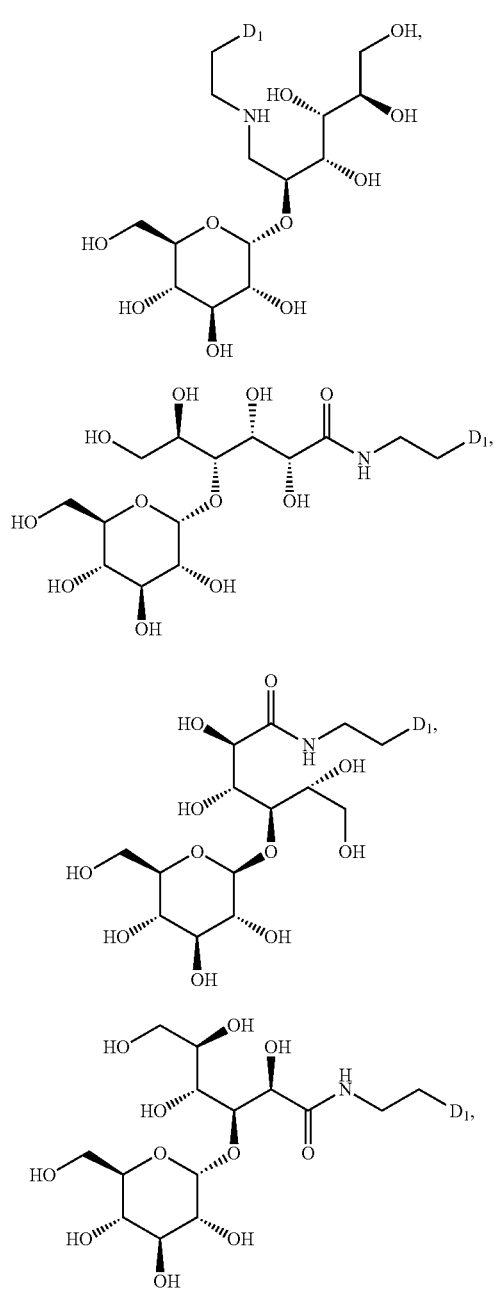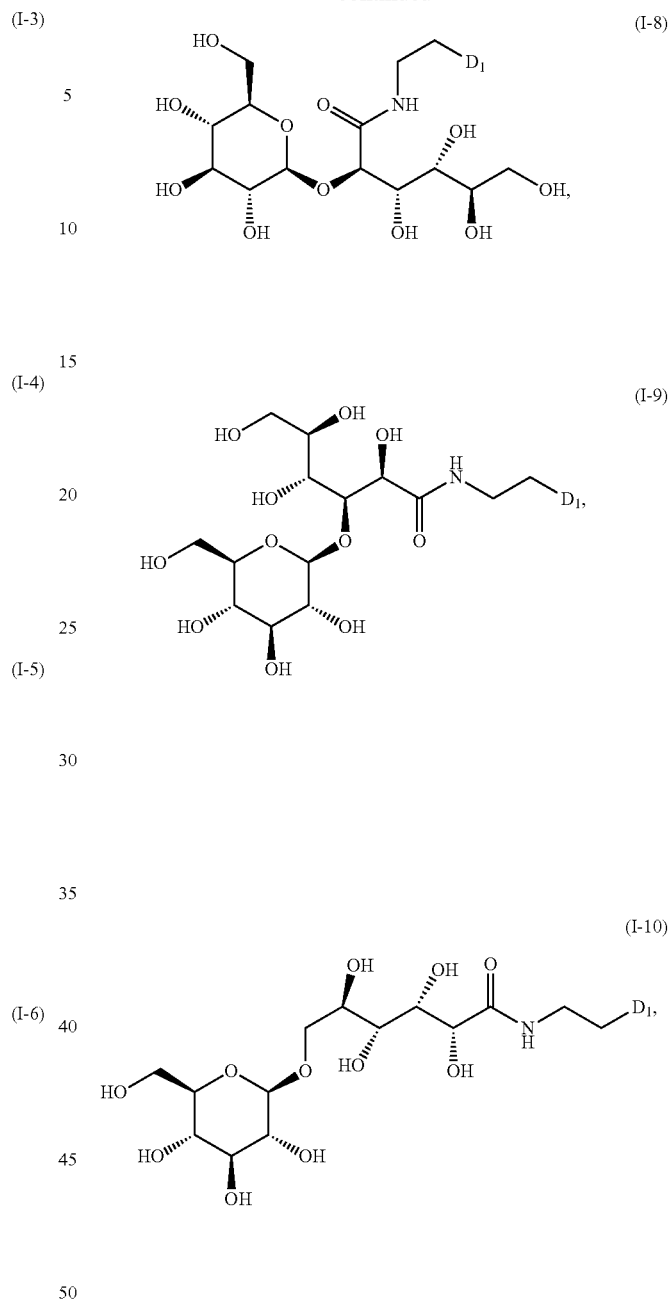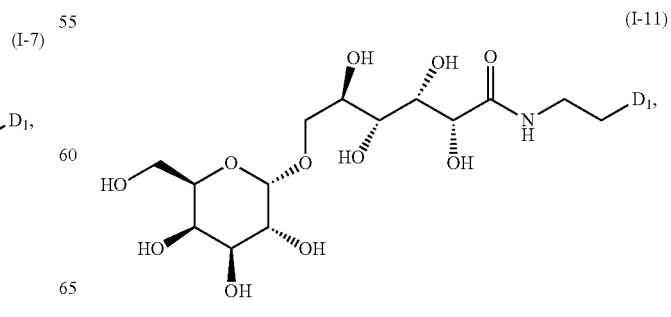

(I-12)
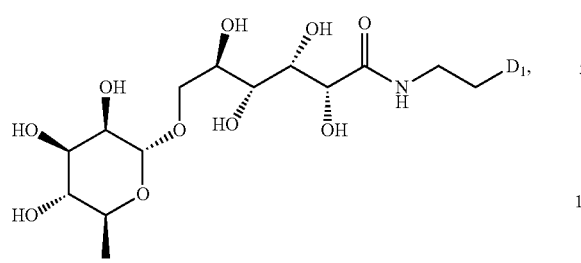
(I-13)
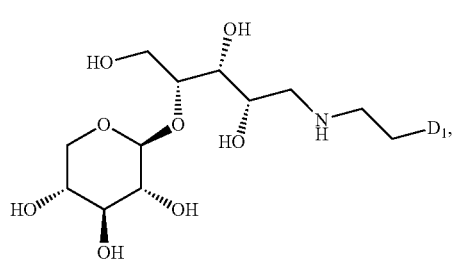
(I-14)
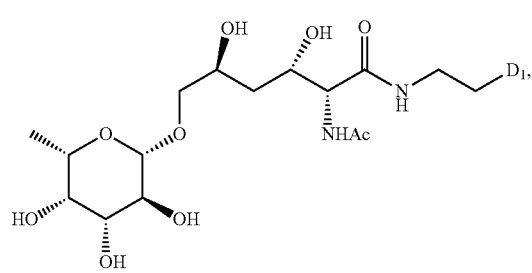
(I-15)
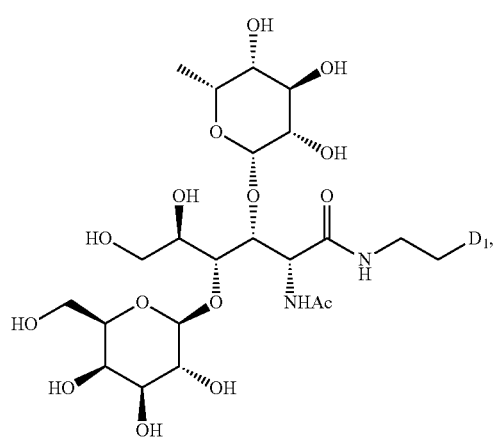
(I-16)
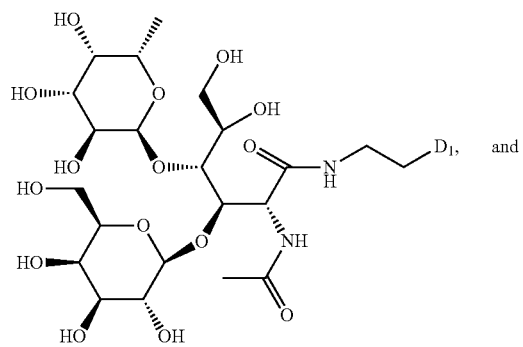
(I-17)
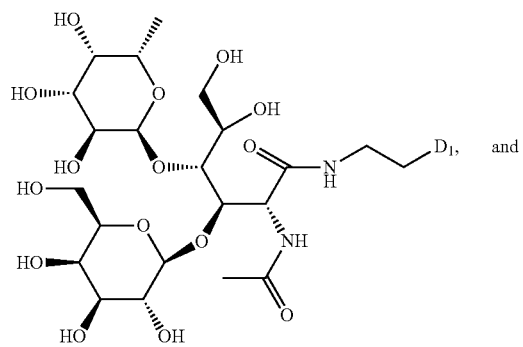
In some embodiments, the compound has the structure of Formula (II),

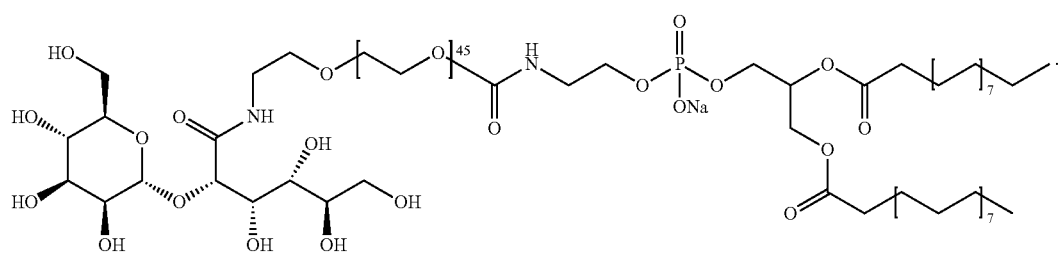

In another aspect, a pharmaceutical composition is described, including the compound described in any of the preceding embodiments and a pharmaceutically acceptable excipient.

In some embodiments, the composition further includes a nanocarrier.

In some embodiments, the composition further includes an active substance.

In some embodiments, the composition further includes the active substance is an immunomodulator.

In some embodiments, the immunomodulator is selected from DNA, tRNA, siRNA, viral particle, protein, peptide, carbohydrate, glycoprotein, glycopeptides, proteoglycan, cell extract, hydrophilic drug, hydrophobic drug, B-cell antigen, T-cell antigen, antigen of a fungal, protozoan, parasitic organism, synthetic lipid, mineral, vegetal lipid, saponine, and mixtures thereof.

In some embodiments, the nanocarrier is formed by a phospholipid.

In some embodiments, the nanocarrier is a liposome.

In some embodiments, the nanocarrier is a micelle.

In some embodiments, the nanocarrier is a synthetic nanocarrier.

In some embodiments, the nanocarrier is selected from the group consisting of niosome, lipoprotein, carbon nanotube, nanocapsule, nanocrystal, silicon nanoparticle, calcium phosphate, ciclodextrin, metallic nanoparticle, dendrimer, protein-core nanoparticle, fullerene, and a mixture thereof.

In yet another aspect, a method of targeted delivery to an antigen-presenting cell is described, including contacting the antigen-presenting cell with at least one compound of any one of the preceding embodiments.

In yet another aspect, a method of targeted delivery to an antigen-presenting cell is described, including contacting the antigen-presenting cell with the composition of any one of the preceding embodiments.

In some embodiments, the antigen-presenting cell is a dendritic cell.

In yet another aspect, a method of treating or preventing a disease or condition susceptible to treatment by immunomodulation is described, including administering the composition of any one of the preceding embodiments to a subject.

In some embodiments, the disease or condition is an infectious disease, cancer, autoimmune disease, or transplant rejection.

BRIEF DESCRIPTION OF THE DRAWINGS

The foregoing and other objects of the present invention, the various features thereof, as well as the invention itself, may be more fully understood from the following description, when read together with the accompanying drawings. The drawings are presented for illustration only and are not intended to limit the invention.

FIGS. 2A-C depict flow cytometry results of DC-targeting by rhodamine-labelled liposomes after 10 minutes of incubation with Manα1-2Man-L and controls to ensure their percentage of specific binding. As compared to the control groups, the dendritic cell uptake of rhodamine liposomes was improved dramatically with Manα1-2Man-L.

FIGS. 3A-C were treated with plain-L. FIGS. 3D-F were treated with Manα1-2Man-rh-L.

FIGS. 4A-C were treated with plain-L. FIGS. 4D-F were treated with Manα1-2Man-rh-L.

DETAILED DESCRIPTION

Figure 1:
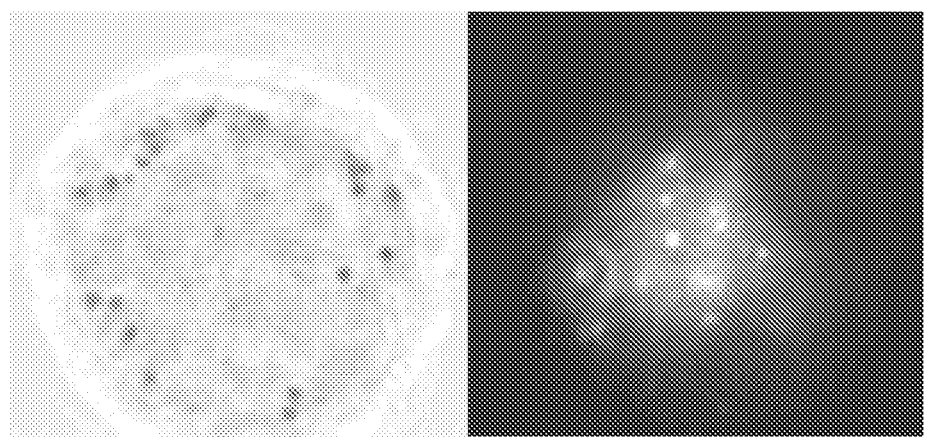
FIG. 1 shows fluorescence microscopy images of dendritic cell uptake of rhodamine-labelled Manα1-2Man-L after 10 minutes of incubation.

The subject matter discloses compounds, pharmaceutical compositions, and methods for targeted IS delivery and modulation of the immune response.

As will be apparent to one of ordinary skill in the art from a reading of this disclosure, the disclosed subject matter can be embodied in forms other than those specifically disclosed herein. The particular embodiments described herein are, therefore, to be considered as illustrative and not restrictive. Those skilled in the art will recognize, or be able to ascertain, using no more than routine experimentation, numerous equivalents to the specific embodiments described herein.

In one aspect, the present disclosure includes a compound having the structure of Formula (I),

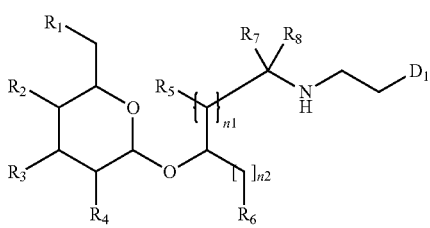

(I)

or a pharmaceutically acceptable salt or hydrate thereof, wherein $R_1$, $R_2$, $R_3$, $R_4$, $R_5$, and $R_6$ are each independently H, OH, O-monosaccharide, NHAc, or Me;

$n_1$ and $n_2$ are each independently 0, 1, 2, 3, or 4, provided that the sum of $n_1$ and $n_2$ is 4;

$R_7$ and $R_8$ are each independently hydrogen, or $R_7$ and $R_8$ together form an oxo (=O); and $D_1$ is a polymer selected from a group consisting of negative polymer, positive polymer, neutral polymer, linear or branched polymer, a lipid, hydrophobic carbon chain, nanoparticle organic molecule, nanoparticle inorganic molecule, drug, ribonucleic acids, peptide-nucleic acids (PNAs), a mixture thereof, and a derivative thereof.

In one embodiment, the present disclosure also relates to pharmaceutical compositions comprising the disclosed components, and pharmaceutically acceptable excipients. In another embodiment, the disclosure relates to methods of targeted delivery to an antigen-presenting cells, comprising contacting the antigen-presenting cell with the disclosed compositions. In another embodiment, method of treating or preventing a disease or condition susceptible to treatment by immunomodulation comprising administering the disclosed compounds.

General

The present disclosure relates to the regulation of the immune system through targeted delivery of the disclosed compounds and an active substance, such as immunomodulators, to an antigen-presenting cell. Examples of immunomodulators include, but are not limited to, DNA, tRNA, siRNA, viral particle, protein, peptide, carbohydrate, glycoprotein, glycopeptides, proteoglycan, cell extract, hydrophilic drug, hydrophobic drug, B-cell antigen, T-cell antigen, antigen of a fungal, protozoan, parasitic organism, synthetic lipid, mineral, vegetal lipid, saponine, and mixtures thereof.

One way to regulate the immune response is through gene therapy, such as by using DNA vaccines that can generate an immune response after cell transfection (Irvine, A. S., et al., *Efficient nonviral transfection of dendritic cells and their use for in vivo immunization*. Nat Biotechnol, 2000. 18(12): p. 1273-8; Landi, A., L. A. Babiuk, and S. van Drunen Littel-van den Hurk, *High transfection efficiency, gene expression, and viability of monocyte-derived human dendritic cells after nonviral gene transfer*. J Leukoc Biol, 2007. 82(4): p. 849-60; Tan, P. H., et al., *Immunolipoplexes: an efficient, nonviral alternative for transfection of human dendritic cells with potential for clinical vaccination*. Mol Ther, 2005. 11(5): p. 790-800; Tan, P. H., et al., *Modulation of human dendritic-cell function following transduction with viral vectors: implications for gene therapy*. Blood, 2005. 105 (10): p. 3824-32). Genetic manipulation upon vaccination (prophylactic or therapeutic vaccines) is a method where the de novo synthesis of the proteins of immunological interest allows their presentation in the context of the major histocompatibility complex (MHC) class I molecules. As a result, a cytotoxic T Lymphocyte (CTL) response could be induced. (Langellotti, C., *Modulación de la respuesta inmune a través del uso de inmunomoduladores incluidos en una vacuna génica*, in *Facultad de Ciencias Exactas, Químicas y Naturales*. 2007, Universidad de Morón: Morón. p. 102; Riedl, P., J. Reimann, and R. Schirmbeck, *Peptides containing antigenic and cationic domains have enhanced, multivalent immunogenicity when bound to DNA vaccines*. J Mol Med, 2004. 82(2): p. 144-52; Schirmbeck, R., et al., *Antigenic epitopes fused to cationic peptide bound to oligonucleotides facilitate Toll-like receptor 9-dependent, but CD4+ T cell help-independent, priming of CD8+ T cells*. J Immunol, 2003. 171(10): p. 5198-207.

An alternative to immune therapy is the targeting of various cargoes (such as siRNA, new developed drugs or specific proteins and peptides that can be used as antigens or for their effector properties, for example, pro apoptotic peptides) into specific cells of the IS, by vehicularizing them in nanocarriers or targeting molecules. These molecules, used alone or together, can trigger a desired response in DC that can lead them to activation or anergy. To treat diseases such as cancer, in addition to a humoral response, a strong CTL response is needed. To treat autoimmune diseases, an anergy towards self antigens is needed.

By transfecting DC or delivering antigen directly to DC cytoplasm, it is possible to process the de novo synthesized or uptaked proteins as endogenous antigen, and the resulting peptides are presented under the MHC I context, priming $CD8^+$ T lymphocytes to generate specific cytotoxic immune responses. These responses are desirable against some intracellular pathogens such as certain viruses (eg. HIV, HBV, HCV, hepesviruses) and cancer.

By using transfected DC or antigen-pulsed DC plus specific molecules such as various co-stimulatory signals, anergy can be induced against the desired antigen to treat conditions such as autoimmune disease or transplant rejection. To obtain such results during a therapy, specific tools are needed to manipulate the immune response by manipulating specific cells, such as APC cells like dendritic cells. It has been demonstrated that APC can be efficiently transfected with the aid of nanotechnological carriers such as liposomes (Pappalardo, J. S., et al., J Control Release, 134(1): pp. 41-6 (2009); Landi, 2007).

Figure 7:
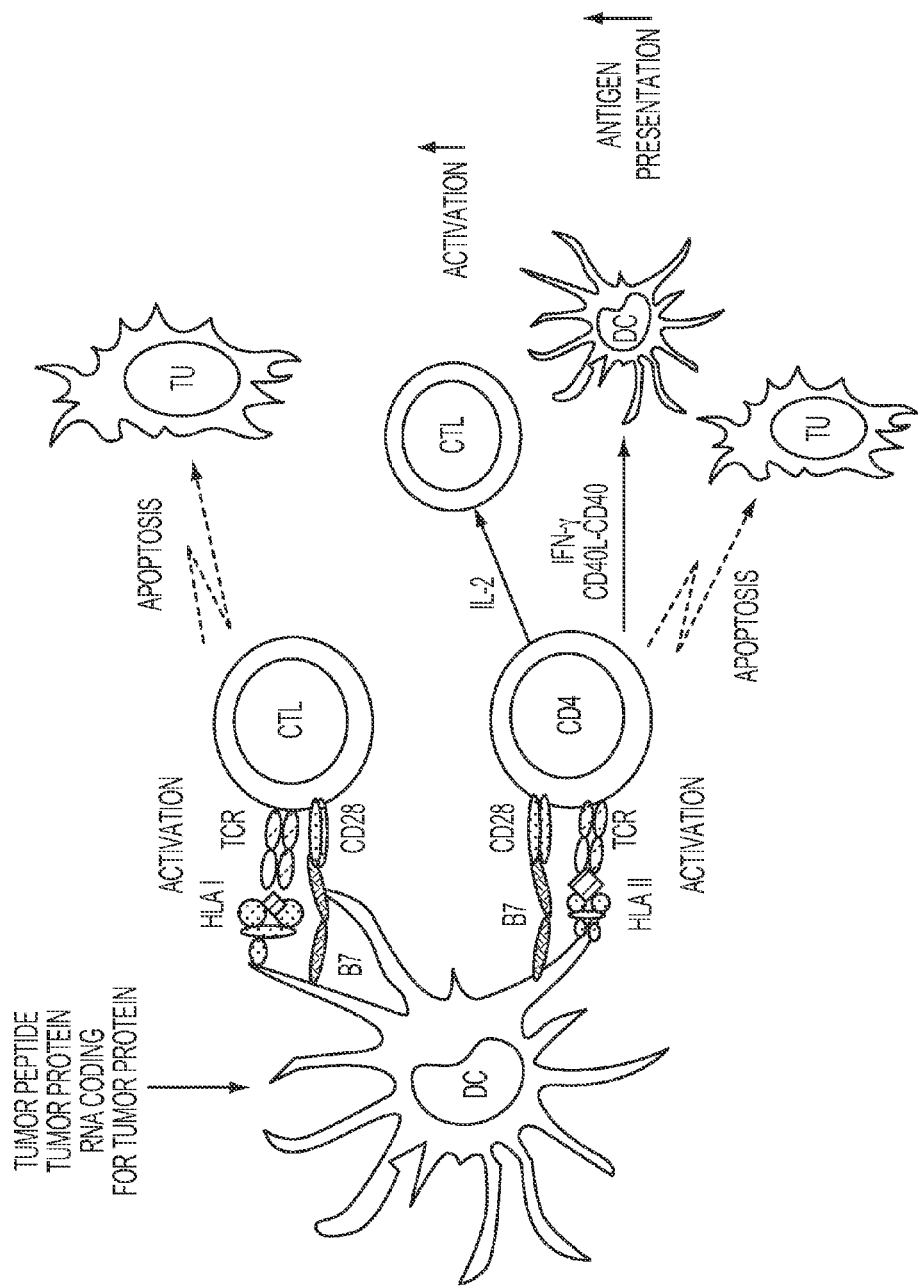
FIG. 7 is a graphical representation of DC-based immunotherapeutic strategies for prostate cancer.

The use of dendritic cells (DC) for the development of, for example, prophylactic vaccines against infectious diseases and/or therapeutic cancer vaccines is attractive because of their unique ability to present tumor epitopes via the MHC class I pathway to induce cytotoxic CD8+ T lymphocyte responses (FIG. 7). DCs display a unique capacity to induce and maintain T-cell responses and can be used for vaccination strategies in prostate cancer therapy. DCs are loaded with PCa-associated antigen-derived peptides, protein, or RNA. Due to their high surface expression of HLA-peptide-complexes and co-stimulatory molecules, DCs efficiently activate and expand CD8+ CTLs and CD4+ T cells. CD8+ CTLs possess a profound capability to recognize and destroy tumor cells. CD4+ T cells enhance the capacity of DCs to induce CTLs by the interaction between CD40 on DCs and CD40 ligand on activated CD4+ T cells. In addition, they provide help for the maintenance and expansion of CTLs by secreting cytokines and are able to eradicate tumor cells directly. CTLs: cytotoxic T cells; DCs: dendritic cells; HLA: human leukocyte antigen; IL: interleukin; IFN: interferon; TCR: T cell receptor; TU: tumor cells. See, e.g., Dendritic cell-based immunotherapy for prostate cancer. Füssel et al., M. CLIN DEV IMMUNOL. 2010; 2010:517493. Epub 2010 Nov. 4. Review.)

One of the challenges in immune therapy is manipulation of the cells that direct the immune response. Attempts at DNA transfection have been used to address this issue, but the biggest difficulty has been the resistance of these cells to non-viral transfection techniques (Irvine, 2000; Landi, 2007; Tan, MOL THER, 2005, 11(5): p. 790-800; Tan, BLOOD, 2005, 105(10): p. 3824-32; Tan, BLOOD, 2005. 106(9): p. 2936-43), since they are specialized endocytic cells able to degrade antigens, DNA, RNA, etc. (Marshak-Rothstein, A., Nat Rev Immunol, 2006. 6(11): p. 823-35; Medzhitov, R., Nat Rev Immunol, 2001. 1(2): p. 135-45; Sandor, F. and M. Buc, Folia Biol (Praha), 2005. 51(5): p. 148-57; Sandor, F. and M. Buc, Folia Biol (Praha), 2005. 51(6): p. 198-203; Sandor, F. and M. Buc, Folia Biol (Praha), 2005. 51(6): p. 188-97; Yoshikawa, T., et al., Biol Pharm Bull, 2006. 29(1): p. 105-9). Moreover, manipulation of DC in vitro and in vivo is difficult because they are very sensitive to various molecules that can be toxic to them (Irvine 2000; Landi 2007; Tan, Mol Ther, 2005, 11(5): p. 790-800). For that reason, it is also a problem to pulse DC directly with the molecules that are needed for specific therapies.

DC have different specific surface molecules, so-called pattern recognition receptors (PRRs), that recognize pathogen-associated molecular patterns (PAMPs). These PRRs can be the target to send specifically different cargoes to DC (Marshak-Rothstein, 2006; Medzhitov, 2001; Sandor, Folia Biol (Praha), 2005. 51(5): p. 148-57; Sandor, Folia Biol (Praha), 2005 51(6): p. 198-203; Sandor, Folia Biol (Praha), 2005. 51(6): p. 188-97; Kapsenberg, M. L., *Dendritic-cell control of pathogen-driven T-cell polarization*. Nat Rev Immunol, 2003. 3(12): p. 984-93; Modlin, R. L., *Immunology. A Toll for DNA vaccines*. Nature, 2000. 408(6813): p. 659-60; Williams, R. L. and S. Urbe, *The emerging shape of the ESCRT machinery*. Nat Rev Mol Cell Biol, 2007. 8(5): p. 355-68; Yewdell, J. W., E. Reits, and J. Neefjes, Nat Rev Immunol, 2003. 3(12): p. 952-61). It has been described that the disaccharide Manα1-2Man can be found in bigger oligosaccharides, which are PAMPs, as a terminal end in many pathogen surface proteins. These terminal ends (Manα1-2Man) are specifically recognized by a DC PRR called DC-SIGN (Guo, Y., et al., Nat Struct Mol Biol, 2004. 11(7): p. 591-8; Meschi, J., et al., J Gen Virol, 2005. 86(Pt 11): p. 3097-107; Hakkarainen, B., et al., Magn Reson Chem, 2007. 45(12): p. 1076-80; Feinberg, H., et al., J Biol Chem, 2007. 282(6): p. 4202-9; Hong, P. W., et al., J Virol, 2002. 76(24): p. 12855-65; Calarese, D. A., et al., Proc Natl Acad Sci USA, 2005. 102(38): p. 13372-7).

Former approaches used complex chemistry, and percentages of specific binding has not been found in the literature. Some have used bromination and debromination to protect different functional groups of the dimmanose, which makes the procedure more expensive, with many steps and a low recovery of the final product. Others have used different strategies, such as the use of different buffers to link the sugar with a linker protein (not desirable since this protein can generate immune response and sometimes this is not the purpose of the vehicle) with various steps of filtration. In all cases, others have worked with the "circularized" dimannose, meaning that the final product keeps the original hexose cyclic form.

In the instant disclosure, in some embodiments, we disclose the design and synthesis of various compounds. We have shown by fluorescent microscopy and flow cytometry that fluorescent-labeled liposomes containing α1-2 dimannose derivatives were taken up by DC in a specific manner. These compounds as well as other disclosed compounds can be used to target DC-SIGN that are used to induce uptake of, for example, various antigens as well as nucleic acids by DC.

Compounds

The present disclosure relates to compounds with the structure of Formula (I),

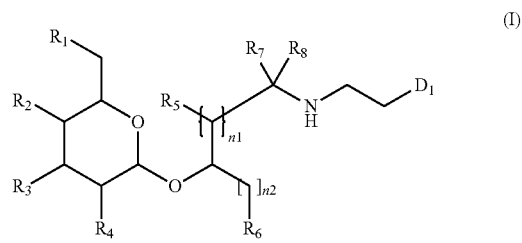

or a pharmaceutically acceptable salt or hydrate thereof, wherein $R_1$, $R_2$, $R_3$, $R_4$, $R_5$, and $R_6$ are each independently H, OH, O-monosaccharide, NHAc, or Me;

$n_1$ and $n_2$ are each independently 0, 1, 2, 3, or 4, provided that the sum of $n_1$ and $n_2$ is 4;

$R_7$ and $R_8$ are each independently hydrogen, or $R_7$ and $R_8$ together form an oxo (=O); and $D_1$ is a polymer selected from a group consisting of negative polymer, positive polymer, neutral polymer, linear or branched polymer, a lipid, hydrophobic carbon chain, nanoparticle organic molecule, nanoparticle inorganic molecule, drug, ribonucleic acids, peptide-nucleic acids (PNAs), a mixture thereof, and a derivative thereof.

In one embodiment, $D_1$ is a peptide or a protein. In another embodiment, the $D_1$ is a polymer selected from the group consisting of a derivative of nylon, PVC, silicone, latex, polyvinyl butyral, polyacrylonitrile, polystyrene, polyethylene, polyethyleneglycol (PEG), polyethyleneoxide (PEO), polyethyleneimine (PEI), polyoxymethylene (POM), a mixture thereof, and a derivative thereof. In another embodiment, $D_1$ is a PEG derivative selected from the group consisting of PEG (poly(ethylene glycol)), PEG-DSPE, PEGCer (PEG-ceramide), PEGCerC14 (PEGCer containing a 14-carbon fatty acyl chain), PEGCerCzo (PEGCer containing a 20-carbon fatty acyl chain), PEG-COOH (carboxylated PEG-derivative), PEG-PE (poly(ethylene glycol)phosphatidylethanolamine), and PEG-Osu (poly(ethyelene glycol)hydroxysuccinimide ester).

In another embodiment, the PEG derivative is selected from the group consisting of PEG-DSPE, PEG-DPPE, PEG-DOPE, PEG-DMPE, PEG-ceramide, fluorescent PEG-DSPE derivative, Succinyl-PEG, Carboxylic Acid-PEG, Maleimide-PEG, PDP-PEG, Amine-PEG, Biotin-PEG, Cyanur-PEG, Folate-PEG, a mixture thereof, and a derivative thereof. In another embodiment, the PEG-ceramide is selected from the group consisting of octanoyl-sphingosine, palmitoyl-sphingosine, and a mixture thereof. In another embodiment, the fluorescent PEG-DSPE derivative is carboxyfluorescein-PEG-DSPE.

In other embodiments, the compounds have the following structures:

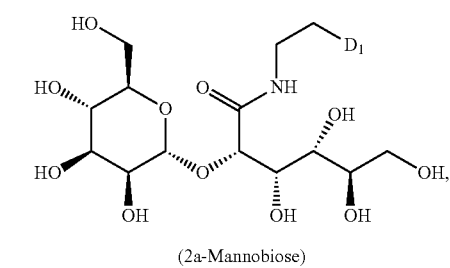
(2a-Mannobiose) (I-1)
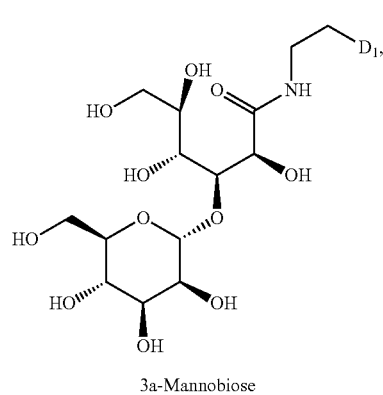
3a-Mannobiose (I-2)
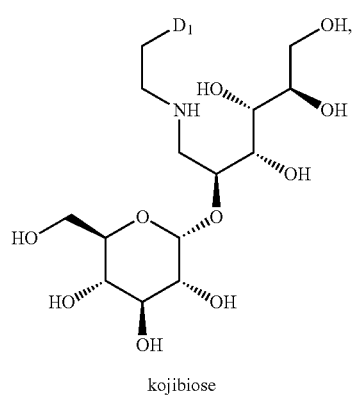
kojibiose (I-3)
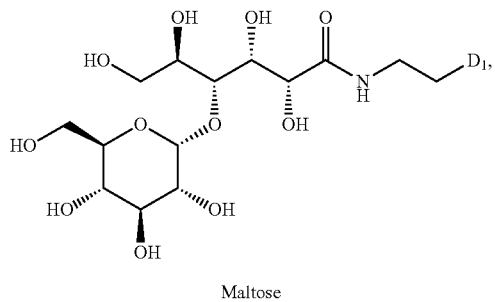
Maltose (I-4)
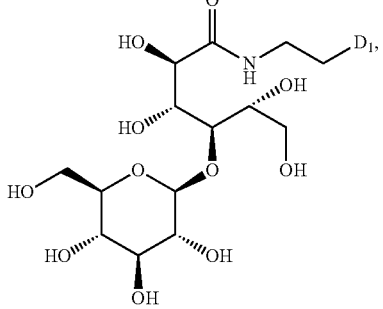
cellobiose (I-5)
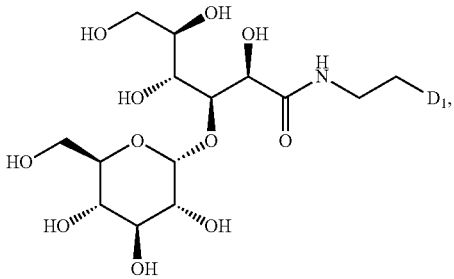
Nigerose (I-6)
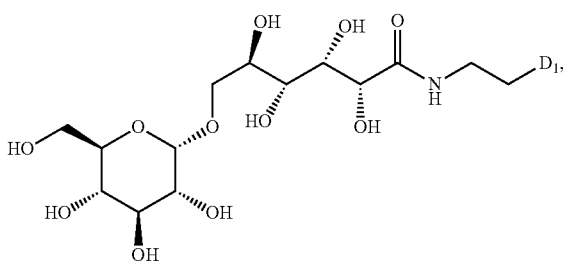
isomaltose (I-7)
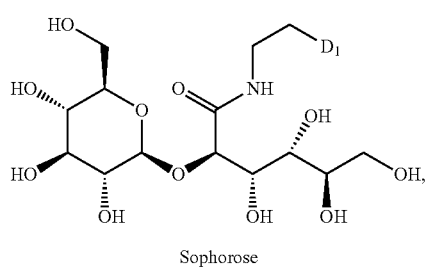
Sophorose (I-8)
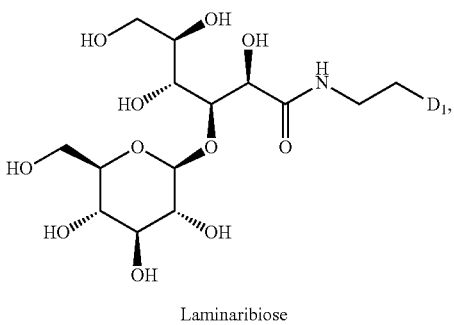
Laminaribiose (I-9)

-continued
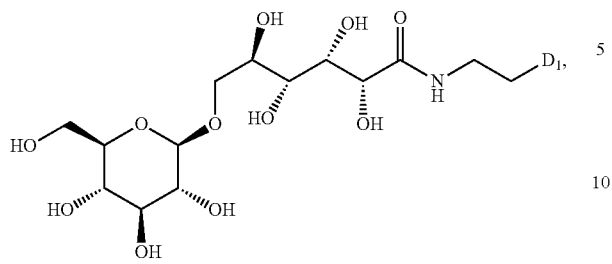
Gentiobiose (I-10)
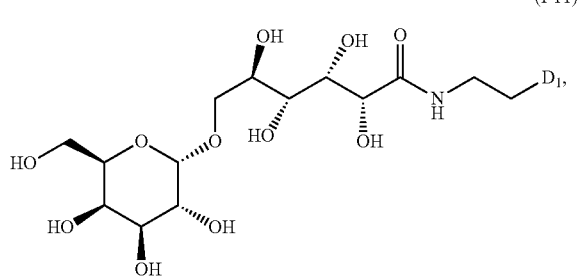
Meliobiose (I-11)
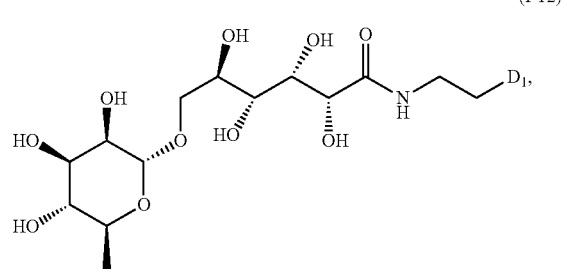
Rutinose (I-12)
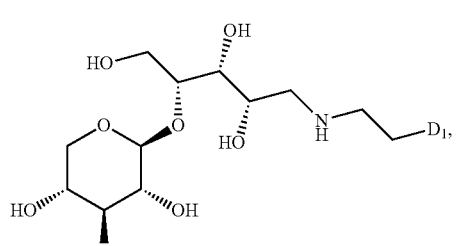
Xylpbiose (I-13)
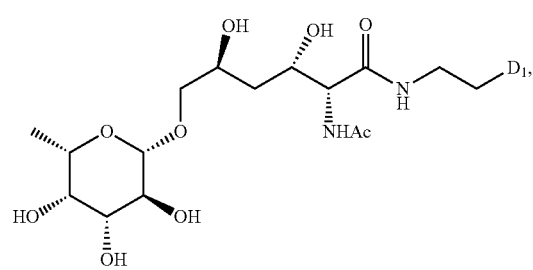
Fucα1-4GlcNAc (I-14)
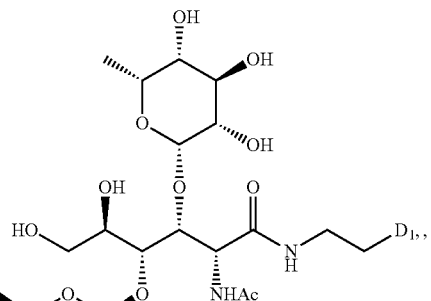
(I-15)
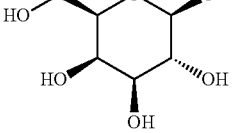
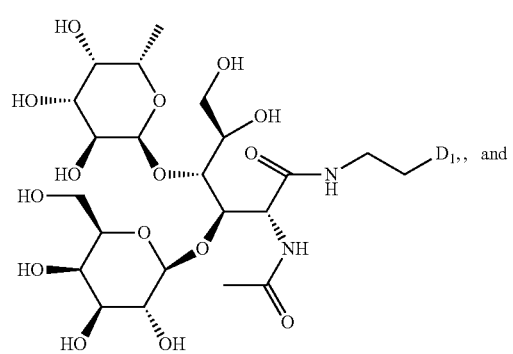
Lewis a (I-16)
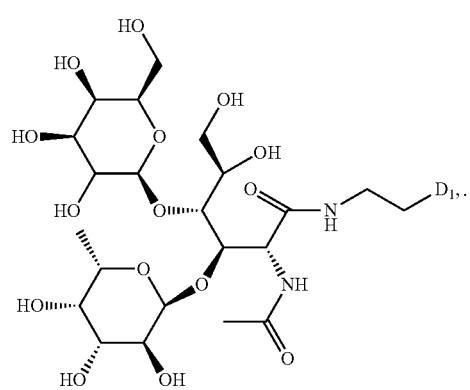
Lewis x (I-17)
In another aspect, the compound has the structure of Formula (II),

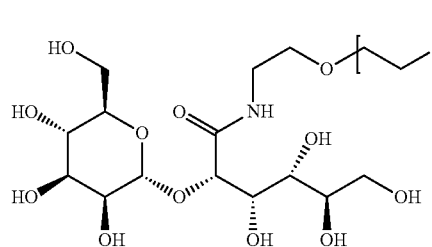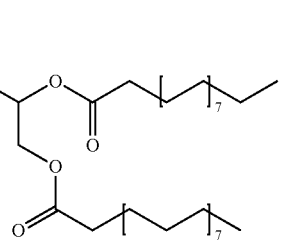

Pharmaceutical Compositions

In one aspect, pharmaceutical compositions with the disclosed compounds and a pharmaceutically acceptable excipient are disclosed.

In another aspect, the disclosure includes a method of treating or preventing a disease or condition susceptible to treatment by immunomodulation comprising administering the pharmaceutical composition to a subject. In one embodiment, the disease or condition is an infectious disease, cancer, autoimmune disease, or transplant rejection.

The pharmaceutical compositions of the present disclosure can be specially formulated for administration in solid or liquid form, including but not limited to those adapted for the following: (1) oral administration, for example, drenches (aqueous or non-aqueous solutions or suspensions), tablets, boluses, powders, granules, pastes for application to the tongue; or (2) parenteral administration, for example, by subcutaneous, intramuscular or intravenous injection as, for example, a sterile solution or suspension.

The "pharmaceutically acceptable excipient" is "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term "carrier" denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency.

As discussed herein, certain embodiments of the present pharmaceutical agents may be provided in the form of pharmaceutically-acceptable salts. The term "pharmaceutically-acceptable salt," in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., (1977) "Pharmaceutical Salts", *J. Pharm. Sci.* 66:1-19.)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. Representative organic amines useful for the formation of base addition salts include ethylamine, diethylamine, ethylenediamine, ethanolamine, diethanolamine, piperazine and the like. (See, for example, Berge et al., supra.)

Wetting agents, emulsifiers and lubricants, such as sodium lauryl sulfate, magnesium stearate, and polyethylene oxide-polybutylene oxide copolymer as well as coloring agents, release agents, coating agents, sweetening, flavoring and perfuming agents, preservatives and antioxidants can also be present in the compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Administration to a Subject

Some aspects of the invention involve administering an effective amount of a composition to a subject to achieve a specific outcome. The small molecule compositions useful according to the methods of the present invention thus can be formulated in any manner suitable for pharmaceutical use.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode allowing the compound to be taken up by the appropriate target cells. "Administering" the pharmaceutical composition of the present invention can be accomplished by any means known to the skilled artisan. Specific routes of administration include but are not limited to oral, transdermal (e.g., via a patch), parenteral injection (subcutaneous, intradermal, intramuscular, intravenous, intraperitoneal, intrathecal, etc.), or mucosal (intranasal, intratracheal, inhalation, intrarectal, intravaginal, etc.). An injection can be in a bolus or a continuous infusion.

For example, the pharmaceutical compositions according to the invention are often administered by intravenous, intramuscular, or other parenteral means, or by biolistic "gene-gun" application to the epidermis. They can also be administered by intranasal application, inhalation, topically, orally, or as implants, and even rectal or vaginal use is possible. Suitable liquid or solid pharmaceutical preparation forms are, for example, aqueous or saline solutions for injection or inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer R (1990) *Science* 249:1527-33, which is incorporated herein by reference.

The concentration of compounds included in compositions used in the methods of the invention can range from about 1 nM to about 100 µM. Effective doses are believed to range from about 10 picomole/kg to about 100 micromole/kg.

The pharmaceutical compositions are preferably prepared and administered in dose units. Liquid dose units are vials or ampoules for injection or other parenteral administration. Solid dose units are tablets, capsules, powders, and suppositories. For treatment of a patient, depending on activity of the compound, manner of administration, purpose of the administration (i.e., prophylactic or therapeutic), nature and severity of the disorder, age and body weight of the patient, different doses may be necessary. The administration of a given dose can be carried out both by single administration in the form of an individual dose unit or else several smaller dose units. Repeated and multiple administration of doses at specific intervals of days, weeks, or months apart are also contemplated by the invention.

The compositions can be administered per se (neat) or in the form of a pharmaceutically acceptable salt. When used in medicine the salts should be pharmaceutically acceptable, but non-pharmaceutically acceptable salts can conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Compositions suitable for parenteral administration conveniently include sterile aqueous preparations, which can be isotonic with the blood of the recipient. Among the acceptable vehicles and solvents are water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono- or diglycerides. In addition, fatty acids such as oleic acid find use in the preparation of injectables. Carrier formulations suitable for subcutaneous, intramuscular, intraperitoneal, intravenous, etc. administrations can be found in *Remington's Pharmaceutical Sciences*, Mack Publishing Company, Easton, Pa.

The compounds useful in the invention can be delivered in mixtures of more than two such compounds. A mixture can further include one or more adjuvants in addition to the combination of compounds.

A variety of administration routes is available. The particular mode selected will depend, of course, upon the particular compound selected, the age and general health status of the subject, the particular condition being treated, and the dosage required for therapeutic efficacy. The methods of this invention, generally speaking, can be practiced using any mode of administration that is medically acceptable, meaning any mode that produces effective levels of response without causing clinically unacceptable adverse effects. Preferred modes of administration are discussed above.

The compositions can conveniently be presented in unit dosage form and can be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Nanocarrier

In one aspect, the disclosure includes the pharmaceutical composition and a nanocarriers. In one embodiment, the composition further comprises an active substance. The active substance is, for example, an immunomodulator. Immunomodulators include, but are not limited to, DNA, tRNA, siRNA, viral particle, protein, peptide, carbohydrate, glycoprotein, glycopeptides, proteoglycan, cell extract, hydrophilic drug, hydrophobic drug, B-cell antigen, T-cell antigen, antigen of a fungal, protozoan, parasitic organism, synthetic lipid, mineral, vegetal lipid, saponine, and mixtures thereof.

In one embodiment, the nanocarriers is formed by a phospholipids. Nanocarriers suitable for use with the present invention include, but not limited to, a liposome, micelle, synthetic narrier, niosome, lipoprotein, carbon nanotube, nanocapsule, nanocrystal, silicon nanoparticle, calcium phosphate, ciclodextrin, metallic nanoparticle, dendrimer, protein-core nanoparticle, fullerene, and a mixture thereof.

Methods of Targeted Delivery

In one aspect, the disclosure includes a method of targeted delivery to an antigen-presenting cell, comprising contacting the antigen-presenting cell with at least one of the disclosed compounds. In another aspect, the disclosure includes a method of targeted delivery to an antigen-presenting cell, comprising contacting the antigen-presenting cell with at least one of the disclosed pharmaceutical compositions. In one embodiment, the antigen-presenting cell is a dendritic cell.

Methods of Preparation of Compounds

Instead of using complex chemistry, the disclosed compounds use simple chemistry that enables larger-scale industrial production. In one embodiment, the compound has a second mannose (the one linked to the PEG) that is no longer cyclic but oxidized and with a linear loose end. Although not bound by any theory, this might be the cause of the high affinity to the receptor (DC-SIGN according to references), probably due to a sterical property that makes the loose end to interact (carbons 3, 4, 5 & 6 needed to be free as established in references) more freely with the receptor.

The present disclosure has several advantages over former approaches. First, it results in a structure with an open ring with a free loose end that allows it to interact more freely with a receptor. Second, cheaper production of the compounds enables larger-scale industrial production. Finally, the disclosed compounds result in a high percentage of specific binding to DC.

Following are general synthetic schemes for manufacturing compounds of the present invention. These schemes are illustrative and are not meant to limit the possible techniques one skilled in the art any use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety. For example, the following reactions are illustrations but not limitations of the preparation of some of the starting materials and examples used herein.

Schemes A and B describe various methods for the synthesis of intermediates that may be used to prepare compounds of the present invention. Various modifications to these methods may be envisioned by those skilled in the art to achieve similar results to that of the inventors given below.

In certain embodiment, $R_7$ and $R_8$ of compound for Formula (I) together form an oxo (=O) and the resulting compound has Formula (I'). A compound of Formula (I') may be prepared as shown in Scheme A. $D_1$, $R_1$-$R_6$, $n_1$, and $n_2$ are as defined herein.

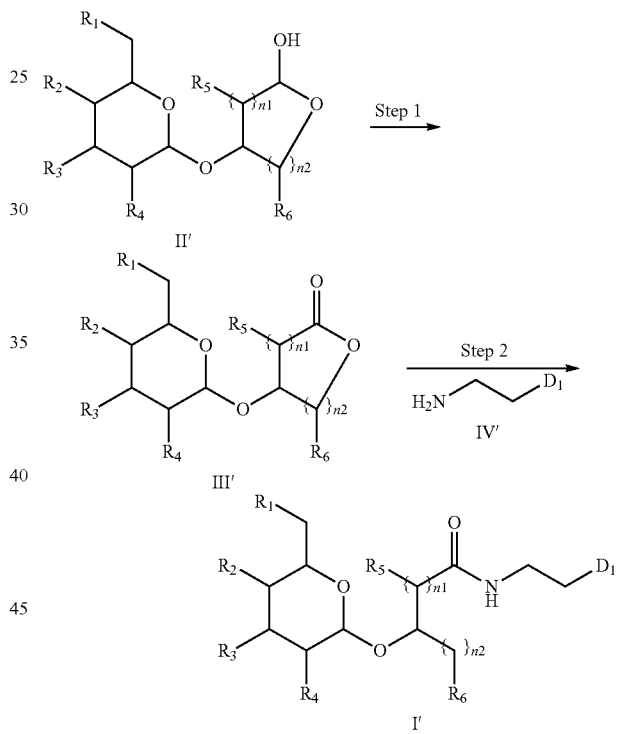

Step 1

Polysaccharide II' may be oxidized to afford ester III'. Suitable solvent for this reaction includes methylene chloride, methanol . . . . Suitable oxidizing agents may include $NaClO_2$, $I_2$, $CrO_3$, and PCC.

Step 2

Ester III' can be reacted with amine treated with amine IV' to afford a compound of Formula I'. Suitable solvent for this reaction includes DMF, DCM, . . . . Suitable base may also be used, including TEA, DIPEA, and pyridine.

In certain embodiment, $R_7$ and $R_8$ of compound for Formula are each H and the resulting compound has Formula (I"). A compound of Formula (I") may be prepared as shown in Scheme B. $D_1$, $R_1$-$R_6$, $n_1$, and $n_2$ are as defined herein.

Scheme B

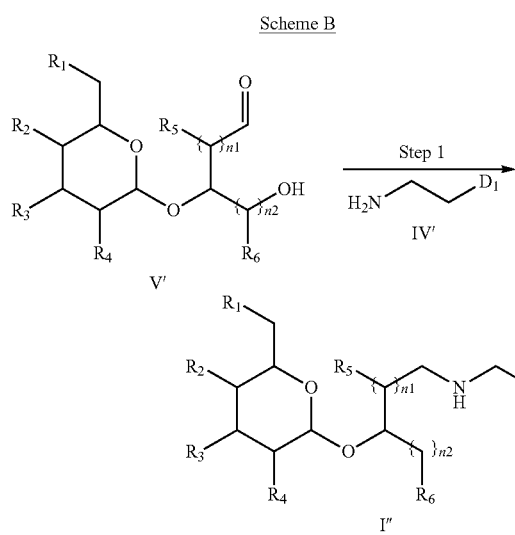

Step 1

Saccharide aldehyde V' may be condensed with amine IV' to afford a compound of Formula I". Suitable solvent for this reaction includes DMF, DCM, Suitable reducing agents may be used, including $NaBH_4$.

Materials

Egg phosphatidylcholine (PC), cholesterol (Chol), 1,2-distearoyl-snglycero-3-phosphoethanolamine-N-[methoxy(poly(ethylene glycol))-2000] (PEG2kDa-DSPE), 1,2-distearoyl-sn-glycero-3-phosphoethanolamine-N-[amino(poly(ethylene glycol))-2000] (NH2-PEG2kDa-DSPE) and 1,2-dioleoyl-sn-glycero-3-phosphoethanolamine-N-(lissamine rhodamine B sulfonyl) (Rh-DOPE) were purchased from Avanti Polar Lipids (Alabaster, Ala.). 2-O-(mannopyranosyl)-D-mannapiranose (Man 1-2Man, FW 342.30) was obtained from V-Labs Inc. (Covington, La.). Amberlite® IR120, triethylamine (TEA), and components of buffer solutions were purchased from Sigma (St. Louis, Mo.). RPMI 1640 medium and heat-inactivated FBS, were supplied by Cellgro (Mediatech Inc., Manassas, Va.). Female BALB/c mice 6-8 weeks old were used (Charles River Laboratories, Wilmington, Mass.). LAB-TEK 4, 8 and 16 well cell culture chambers were purchased from Nunc (Rochester, N.Y.). Murine recombinant GM-CSF (mrGM-CSF) was obtained from R&D Systems (Minneapolis, Minn.). Complete RPMI (comp-RPMI) was prepared with RPMI 1640, 10% FBS, 5.5×10-5M 2-mercaptoethanol (Sigma) and penicillin-streptomycin-amphotericin-B mix solution (Cellgro). Dendritic cell RPMI (DC-RPMI) was prepared with comp-RPMI plus 20 ng/ml of mr-GM-CSF.

Various liposomes were labelled with rhodamine to visualize them. Control plain liposomes (plain-L) were prepared with a mixture of PC:Chol:PEG-PE:Rho-PE and Manα1-2Man-L with PC:Chol:Manα1-2Man-PEG-PE:Rho-PE using a 60:30:2:0.25 molar ratio.

Manα1-2Man-PEG-DSPE was synthesized by oxidation of the anomeric carbon of the second mannose ring (Sch. 1). Once the ring was activated, it was opened through lactonization while being bound to $NH_2$-$PEG_{2kDa}$-DSPE. As a result, the new derivative Manα1-2Man-$PEG_{2kDa}$-DSPE was obtained in which the second mannose remained opened and lineally attached to the PEG-PE (Sch. 2).

Scheme 1. Reaction scheme for the oxidation of the 2-O-α-D-Mannopyranosly-D-mannopyranose (Manα1-2Man).

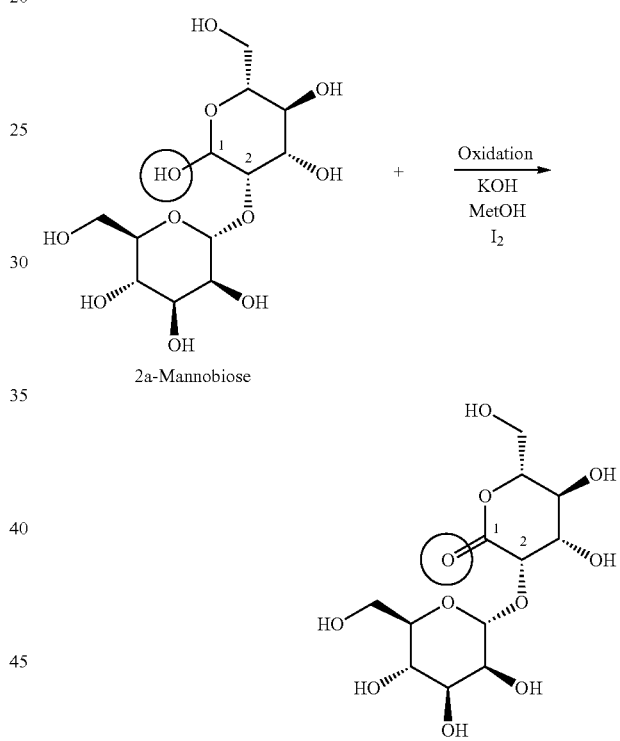

Scheme 2. Reaction scheme for the synthesis of Manα1-2Man-$PEG_{2KDa}$-DSPE.

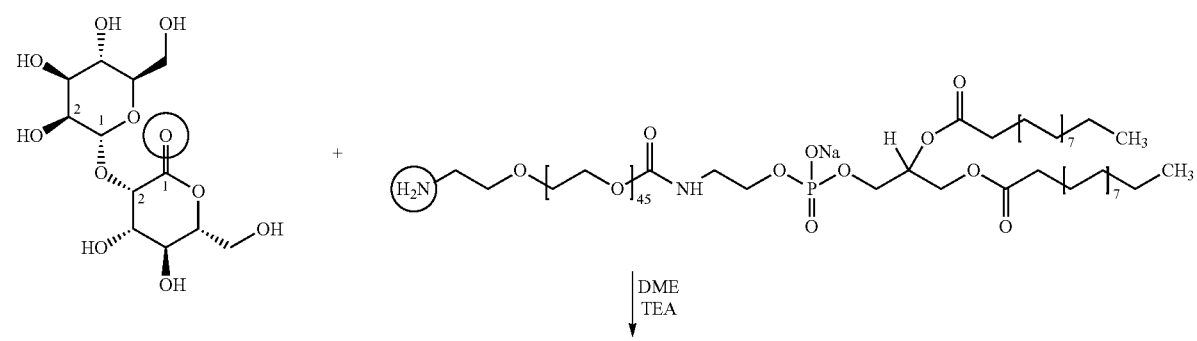

-continued

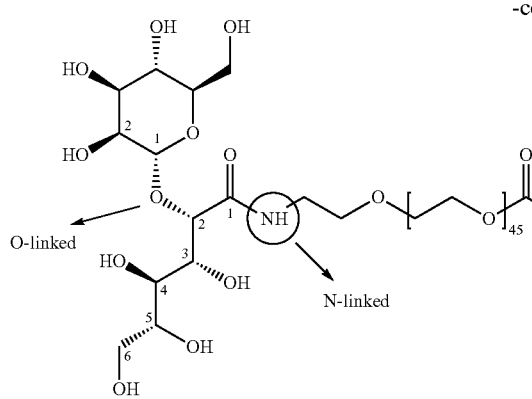

Then, the liposomes were formulated. The size and size distribution were measured by dynamic light scattering (DLS) using a Zeta Plus instrument (Brookhaven Instrument Corporation, Holtsville, N.Y.). The ζ-potential of micelle formulations was measured by a zeta phase analysis light scattering (PALS) with an ultrasensitive zeta potential analyzer instrument (Brookhaven Instruments, Holtsville, N.Y.).

BALB/c mouse DC were generated from bone marrow using mouse recombinant Granulocyte and Macrophage Colony Stimulating Factor (GM-CSF). Cell expression of specific surface molecules (CD11c$^+$/MHC II$^+$) were tested by flow cytometry showing more than 80% of DC purity in the corresponding gate (data not shown).

Synthesis of Manα1-2Man Derivatives

1) Oxidation of Disaccharides:

a) Original Protocol (Kobayashi, K., H. et al., Polym. J., 1985. 17(4): p. 567-575).

Maltose-1-hydrate (12 g, 33 mmol) was dissolved in water (9 ml), diluted with methanol (25 ml), and added to an iodine (17.1 g) solution in methanol (240 ml) at 40° C. At this temperature, a 4% potassium hydroxide solution in methanol (400 ml) was added drop-wise with magnetic stirring for 35 minutes until the color of iodine disappeared. The solution was cooled externally in an ice-bath. The precipitated crystalline product was filtered, washed with cold methanol, and then cold ether, and recrystallized from a mixture (800 ml) of methanol and water (9:1, v:v). Yield was 10.7 g (81%).

The resulting potassium maltonate was then converted to the free acid by passing the aqueous solution through a column of Amberlite IR-120B (H$^+$). The acidic eluate was collected and concentrated in a rotary evaporator. Repeated evaporation of methanol and ethanol solution converted the maltoneic acid into maltonolactone containing a small amount of water in a quantitative yield.

Lactose and maltotriose were oxidized in the same way.

b) Alternative Protocol A.

215 mg of 2-O-(mannopyranosyl)-D-mannapiranose (FW 342.30) were dissolved in 750 μl of water by heating the vial with airdryer. Then, 1.25 ml of methanol was than added. The solution was poured into a round bottomed flask (balloon, possibly with two necks to have one inlet available to add reagents without opening the system) equipped with a reflux condenser and heated up to 40° C.

5 ml of iodine in methanol were added to the solution (302 mg of I2 in 5 ml of methanol) and the solution was stirred for 10 minutes at 40° C. Afterwards, 4% KOH solution in methanol was drop-wise added (10 ml). The addition of KOH provokes the precipitation of various yellowish potassium salts and the oxidized potassium maltonate. KOH solution should be added drop-wise until complete disappearance of the iodine brown color. The mixture was left under stirring for 30 minutes. The mixture was cooled at 4° C. for 1 hour. The precipitate was collected by centrifugation, washed once with methanol, dried under nitrogen flush and dissolved in 2 ml of water. The solution was loaded in a column containing a cationic exchange column Amberlite IR-120 run with mQ water. 100 ml of eluted water was collected and freeze-dried. (the volume of water collected out of the column depend on the length of the column and the amount of cationic resin loaded).

The lyophilized material appeared as a dusty-oily brown product, which was dissolved in 2 ml of methanol and precipitated in ice cold diethylether and washed 4 times with ether. The yellowish powder was desiccated under vacuum in order to remove traces of organic solvent.

c) Alternative Protocol B.

2-O-(mannopyranosyl)-D-mannapiranose (FW 342.30) (5 mg) was dissolved in water (100 μl), diluted with methanol (278 μl), and added to an iodine (7.13 mg) solution in methanol (100 μl) at 40° C. At this temperature, a 4% potassium hydroxide solution in methanol (0.5 ml) was added drop-wise with magnetic stirring for 35 minutes until the color of iodine disappeared. The solution was cooled externally in an ice-bath for 1 hour. The precipitated crystalline product was collected by centrifugation, washed with cold methanol, and then cold ether, dried under nitrogen flush and dissolved in a mixture (0.5 ml) of methanol and water (9:1, v:v). The resulting potassium maltonate was then converted to the free acid by passing the aqueous solution through a column of Amberlite IR-120 (cationic exchange) run with mQ water. The acidic eluate (50 ml) was collected and freeze-dried.

2) Bioconjugation of Manα1-2Man-Lactone with PEG 5 mg of the oxidized mannobiose-lactone (14.7 μmols) were dissolved in 1 ml of methanol. The solution was added of 4 mg (2 μmols) NH$_2$-PEG$_{2kDa}$-DSPE and equimolar amount of trietilamine and kept under stirring at 70° C. at reflux in balloon equipped with reflux condenser for 24 hours. The oxidized disaccharide/PEG-NH$_2$ ratio was 7.8/1 but it can also be 10/1 depending on the availability of the oxidized disaccharide.

These compounds are used for specific DC targeting with nanocarriers carrying one or more active substances, such as an immunomodulator. Immunomodulators include, but are not limited, to DNA, tRNA, siRNA, viral particle, protein, peptide, carbohydrate, glycoprotein, glycopeptides, proteoglycan, cell extract, hydrophilic drug, hydrophobic drug, B-cell antigen, T-cell antigen, antigen of a fungal, protozoan, parasitic organism, synthetic lipid, mineral, vegetal lipid, saponine, and mixtures thereof.

The disclosed compounds can be used with different combinations of drugs and/or plasmids and/or peptides and/or proteins and/or other molecules to generate a strong activation or strong anergy of dendritic cells.

The disclosed compounds can generate an activation of a desired immune response towards some molecules, while others would help in maintaining this response (to prevent or treat infectious disease or cancer). Alternatively, the disclosed compounds could be used as a vehicle of molecules to generate an anergy of a desired immune response towards some molecules while others would help in maintaining this response (to prevent or treat, for example, autoimmune disease or transplant rejection).

H-NMR Characterization

Figure 9A:
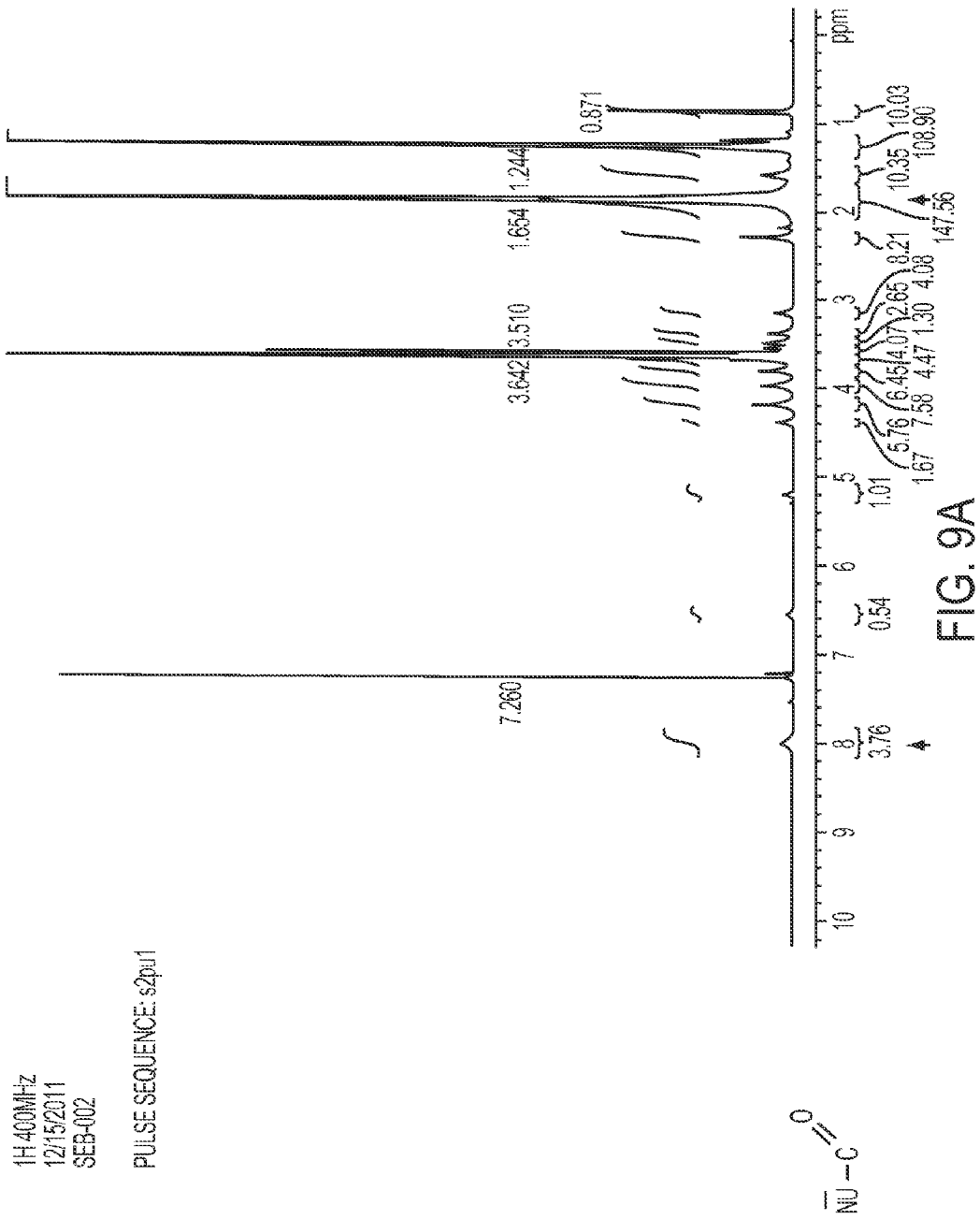
FIG. 9A-B are graphical representation of H-NMR characterization of Manα1-2Man-PEG$_{2KDa}$-DSPE (FIG. 9A) compared to control molecule (FIG. 9B).
Figure 9B:
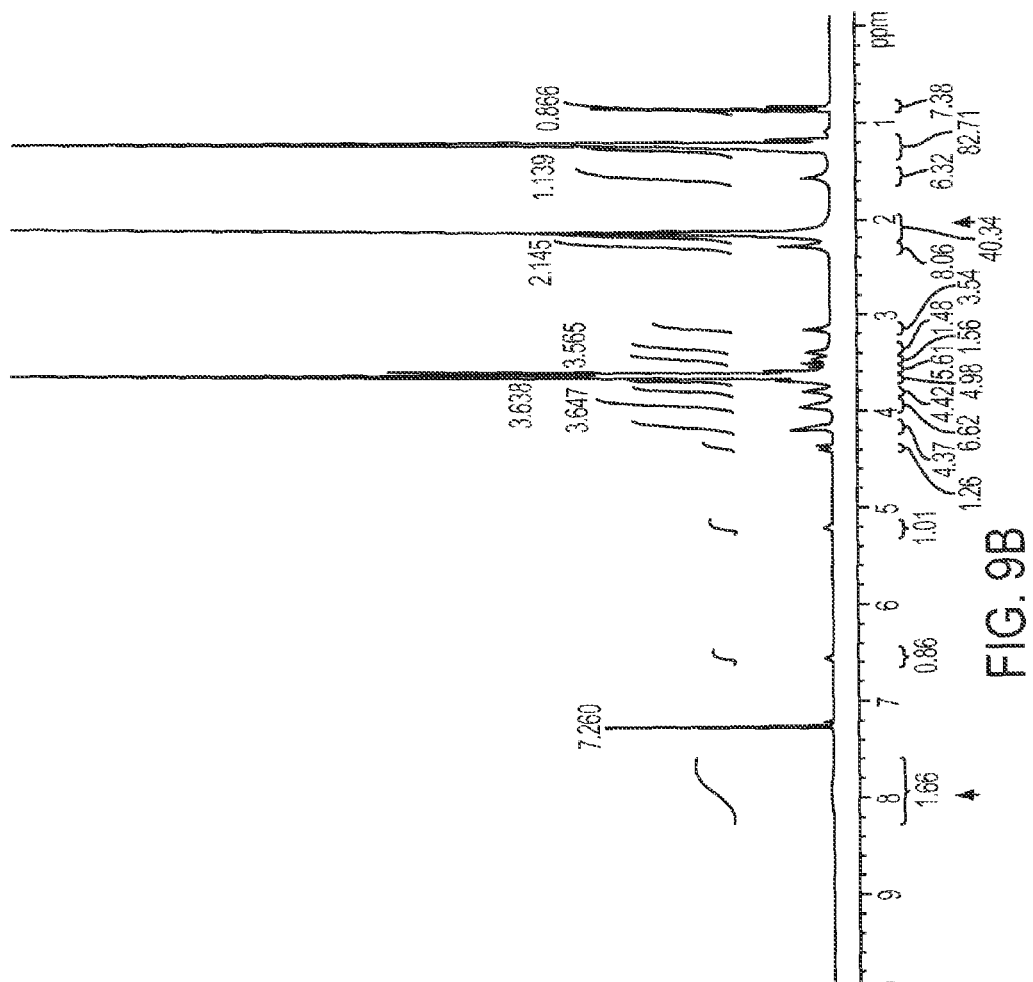

NMR spectroscopy showed that the α1-2 dimannose derivative was formed by the dimannose anchor to the PEG-PE. Arrows indicate differences in NMR reading of Manα1-2Man derivative (FIG. 9A) compared to control molecule (FIG. 9B).

Preparation and Characterization of Liposomes

A lipid film was prepared by rotary evaporation of chloroform from a mixture of PC, Chol and Rh-DOPE (60:30: 0.25 molar ratio). For Manα1-2Man-L, Manα1-2Man-PEG$_{2kDa}$-DSPE was added at 2% molar ratio. For plain-L, PEG$_{2K}$-DSPE was used instead. This film was rehydrated for 30 min in sterile HBS, pH 7.4, at a concentration of 1.78 μg lipid/μl. The suspension was vortexed for 5 min, and then extruded through a polycarbonate filter (pore size, 200 nm) by using a Mini Extruder (Avanti Polar Lipids).

The size of the liposomes was measured by the dynamic light scattering on a Coulter N4 Plus submicron particle analyzer (Beckman Coulter Inc., Fullerton, Calif.). ζ-potential was measured on a ZetaPlus Z-potential analyzer (Brookhaven Instruments Corporation, Holtsville, N.Y.).

Liposomes were characterized on the same day of formulation. Both Manα1-2Man-L and plain-L were around 100 nm size. Manα1-2Man-L were slightly negative compared with control liposomes (Table 1).

TABLE 1

Size and zeta potential of liposomes.

| | Mean size (nm) | Polidiespersity | ζ-potential (mV) |
|---|---|---|---|
| Manα1-2Man-L | 105.6 | 0.131 | −13.79 |
| PlainL | 92.8 | 0.168 | 0 |

Example 1—Liposome-Specific Targeting in Mouse DC

Generation of Bone Marrow-Derived Murine Dendritic Cells

Bone marrow derived DC were obtained as described (Inaba, K., et al., J Exp Med, 1992. 176(6): p. 1693-702) with modifications. Briefly, mice were sacrificed following a protocol approved by Northeastern University Institutional Animal Care and Use Committee in accordance with "Principles of Laboratory Animal Care" (NIH publication N°. 85-23, revised in 1996) and left them for 10 minutes in 70% EtOH. The femurs and tibias were taken with care and placed for 1 minute in 70% EtOH. The epiphysis of each bone were cut and the diaphysis placed in a 5 ml Petri plate with sterile comp-RPMI. Tuberculin syringes were used to perfuse the marrows, inserting the needle in the widest side of the bone and let the media pass through it. Cells were dispersed with a syringe and centrifuged at 1200 rpm for 5 minutes at room temperature. The cell pellet was re-suspended in DC-RPMI to obtain a concentration of $1 \times 10^6$ cels/ml.

The cultures were fed every 48 hours, for 6 days, repeating the same procedure. Gently, the plates were swirled to remove non-adherent granulocytes without dislodging clusters of developing DC that were loosely attached to firmly adherent MØ. Then, 90% of the media was aspirated and placed in a tube. Immediately new DC-RPMI was added very slowly to avoid disrupting the clusters. After the first aspiration (day 2), supernatants with granulocytes were centrifuged at 1200 rpm for 5 minutes at room temperature and re-plated in the same way. Then, at day 6, the aggregates were harvested by trypsinizing them for 5 minutes, with centrifugation afterwards in the same conditions and overnight sub-culture at $3 \times 10^5$ cells/ml in comp-RPMI. From days 7 to 14, the subcultures were fed with comp-RPMI. DC survived and remaining granulocytes died. Plates had remaining firmly adherent cells that could be sub-0cultured in the same plates with comp-RPMI up to 15 days and harvested with spatula.

At day 14 of culture, harvested loosely adherent cells expressed more than 80% double positive CD11c/MHC class II and more than 80% of firmly attached cells were F4/80 positive. In both cases less than 10% Gr-1 positive (data not shown).

Dendritic Cell Uptake of Liposomes

DC uptake, intracellular localization and pathways were studied both in DC treated with Manα1-2Man-L or plain-L. DC were grown in Lab-Tek chambers with a concentration of $2 \times 10^5$ DC per well in 8 well chambers, or $4 \times 10^5$ DC per well in 4-well chambers (equal in surface to 24 well plates, normally used to do transfections) and treated with the different formulations in a serum-free RPMI at 37° C. under 5% $CO_2$. The medium was removed, and the cells washed with sterile PBS, pH 7.4, after 5 minutes of incubation, and fresh comp-RPMI was immediately added. After 15 min of incubation, cells were stained with Hoechst 33342 for 10 min, washed with sterile PBS and re-suspended in comp-RPMI after detaching the chamber. To avoid cell crashing, coverslips with small separators were used, creating a small chamber with living cells. No mounting media was used to avoid artifact. Samples were viewed by epifluorescence microscopy (Nikon Eclipse E400) and evaluated by flow cytometry.

DC uptake of rhodamine-labelled Manα1-2Man-liposomes (Manα1-2Man-L) were done with bone marrow derived mouse DC, as shown in FIG. 1. FIG. 1 shows fluorescence microscopy images of dendritic cell uptake of rhodamine-labelled Manα1-2Man-L after 10 minutes of incubation.

Flow Cytometry

To evaluate the expression of cell-surface molecules, the following antibodies were used: FITC-labeled anti-CD11c, anti-F4/80 (pan MØ marker), and PE-labeled anti-IA$^d$ (MHC class II) and anti-Gr1 (eBioscience, CA, US). Cells were labeled as previously described (Pappalardo, 2009). Briefly, single-cell suspensions ($5 \times 10^5$ cells) were incubated with the indicated antibodies diluted in PBS at 4° C. for 30 min. Then, cells were washed twice with PBS. To evaluate the percentage of specific binding of Manα1-2Man-L or plain-L, DC were acquired and the rhodamine (FL2) was taken in consideration. Analysis was performed using a FACS flow cytometer and CellQuest software (Becton Dickinson, San Jose, Calif.). The results are expressed as MFI.

Liposome-specific targeting was tested in vitro, both by fluorescence microscopy as shown in FIG. 1 and by flow cytometry as shown in FIGS. 2A-C. FIG. 2C shows more than 65% of specific DC targeting, as opposed to 0.92% for untreated DC (FIG. 2A), and 4.93% for plain-L treated DC (FIG. 2B). FIGS. 2A-C depict flow cytometry results of DC-targeting by rhodamine-labelled liposomes after 10 minutes of incubation with Manα1-2Man-L and controls to ensure their percentage of specific binding. As compared to the control groups, the dendritic cell uptake of rhodamine liposomes was improved dramatically with Manα1-2Man-L. Thus, FIGS. 1 and 2A-C show that the cell uptake of rhodamine liposomes was improved dramatically with Manα1-2Man-L in marrow derived DCs.

Figure 8:
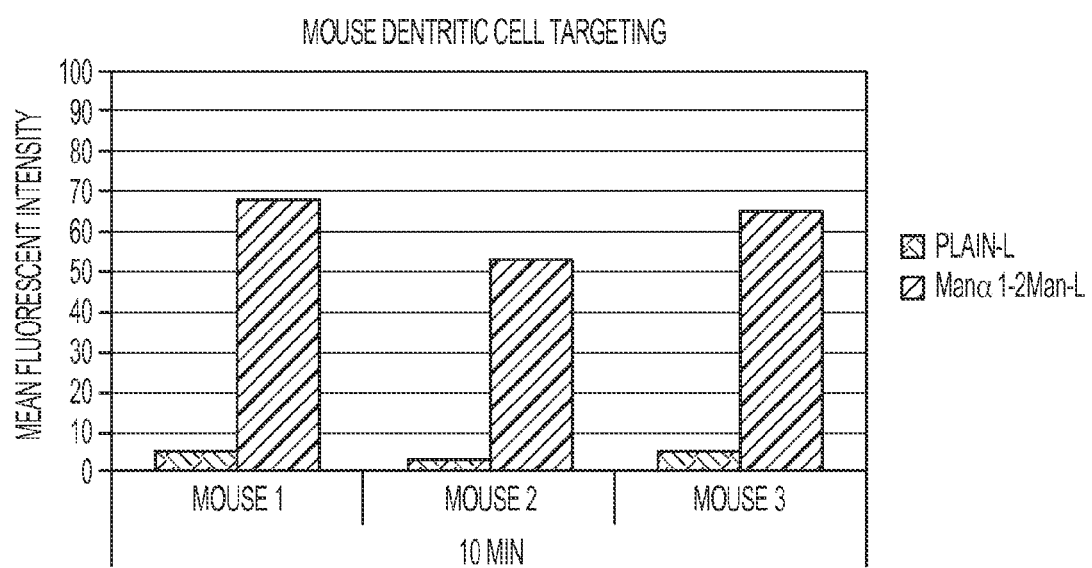
FIG. 8 is a graphical representation of the flow cytometry results in FIGS. 2A-C.

Thus, the results showed by fluorescent microscopy and flow cytometry that fluorescent-labeled liposomes containing Manα1-2Man-L were taken up by DC in a specific manner. When mouse bone marrow derived 4-day old dendritic cell cultures, which are not completely differentiated, were used, more than 65% of specific binding was observed. FIGS. 2A-C show flow cytometry analysis of mouse BMDC treated with rhodamine liposomes. Untreated control showing autofluorescence (FIG. 2A), plain-rh-L (FIG. 2B), and Manα1-2Man-L (FIG. 2C). FIG. 8 is a bar chart of MFI results based on flow cytometry analysis as shown in FIGS. 2A-C.

Figures 3A, 3B, 3C:
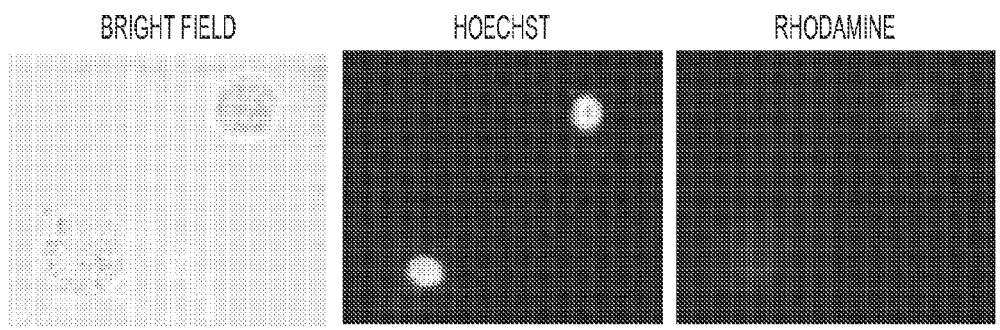
FIGS. 3A-F show fluorescence microscopy of mouse bone marrow-derived dendritic cells (BMDC) treated with rhodamine liposomes at 4 day culture incubated for 10 minutes with rhodmine liposomes.
Figures 3D, 3E, 3F:
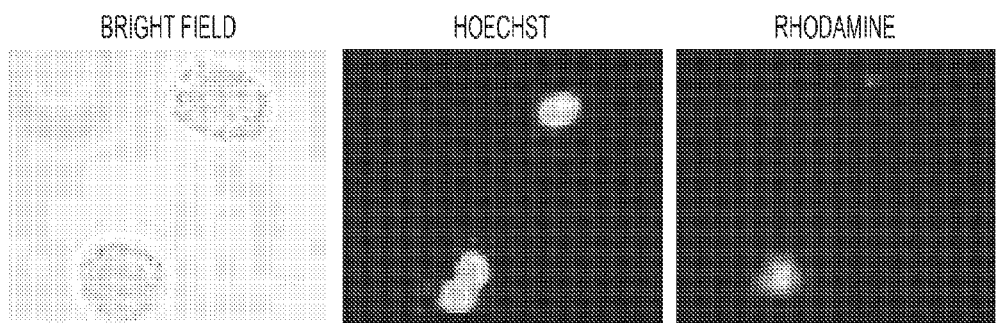

When mouse bone marrow derived 7 day old dendritic cell cultures, which are completely differentiated, were used, only a slight uptake in some dendritic cells was observed. This is explained by DC-SIGN expression in vitro: DC cultures downregulates their expression as the culture becomes differentiated (see FIGS. 3A-F). FIGS. 3A-F show fluorescence microscopy of mouse BMDC treated with rhodamine liposomes at 4 day culture incubated for 10 minutes with rhodamine liposomes. FIGS. 3A-C were treated with plain-L. FIGS. 3D-F were treated with Manα1-2Man-rh-L (2C).

Figure 4A:
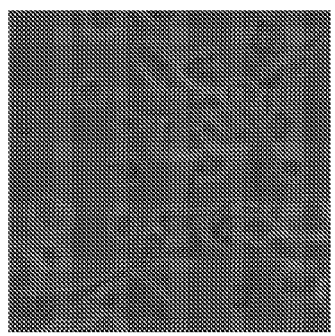
FIGS. 4A-F show fluorescence microscopy of mouse BMDC treated with rhodamine liposomes at 7 day culture incubated for 10 minutes with rhodamine liposomes.
Figure 4B:
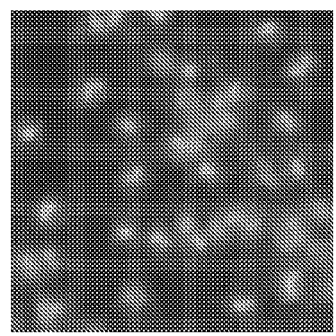
Figure 4C:
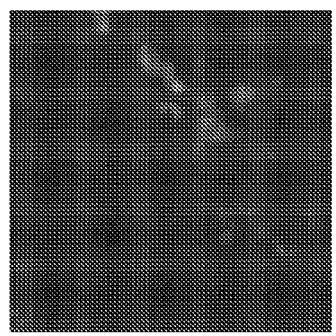
Figure 4D:
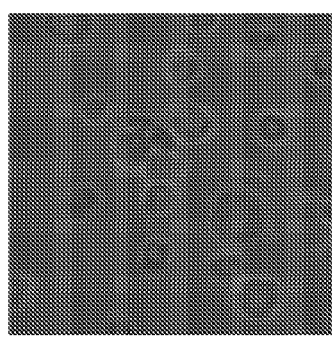
Figure 4E:
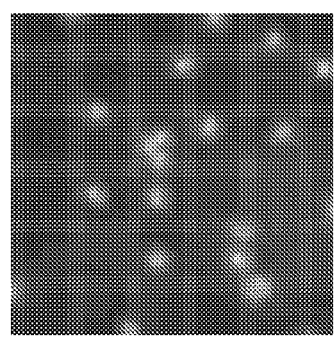
Figure 4F:
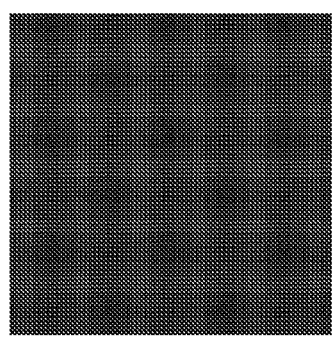

FIGS. 4A-F show fluorescence microscopy of mouse BMDC treated with rhodamine liposomes at 7 day culture incubated for 10 minutes with rhodamine liposomes. FIGS. 4A-C were treated with plain-L. FIGS. 4D-F were treated with Manα1-2Man-rh-L (2C).

In summary, the results in mouse models show an improvement in liposome uptake using the Manα1-2Man-L-treated compounds.

Example 2—Liposome-Specific Targeting in Human DC

Generation of Human Monocyte-Derived Dendritic Cells

Human monocyte derived dendritic cells were prepared following the protocol described herein with good expression levels of specific cell markers. Both under microscope (morphology) and under flow cytometry analysis (forward scatter versus side scatter) cell characteristics were appropriated for HMDC.

In vitro experiments with human DC were performed. We used human DC cultures from two blood donors, and showed the ability of Manα1-2Man-L to target human DC in a specific manner. After 24 hours of treatment with liposomes (10 minutes with serum-free medium and 24 hours with complete medium), the Mean Fluorescence Intensity using Manα1-2Man-L compounds was higher compared to using plain-L (ΔMFI of 50 and 70 for Donors 1 and 2, respectively).

Figure 5:
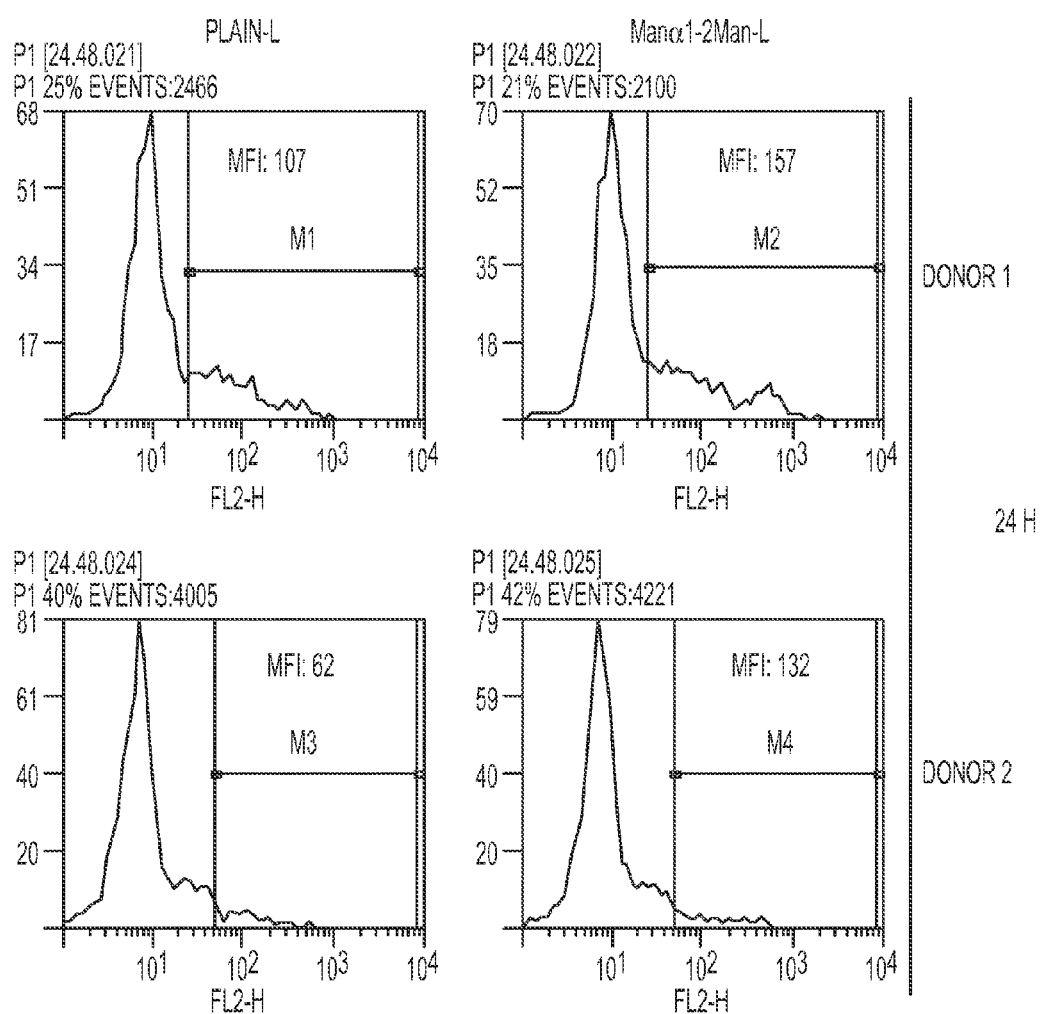
FIG. 5 shows the flow cytometry results from in vitro liposome-specific targeting experiments in human DC cultures. Data is show in Mean Fluorescence Units (MFI) for the two donors.
Figure 6:
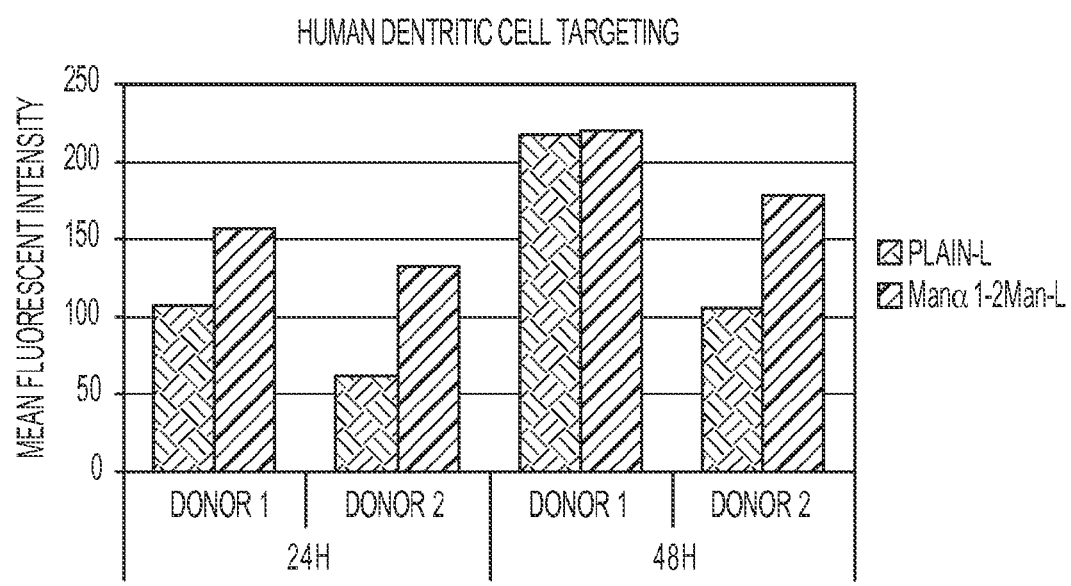
FIG. 6 is a graphical representation of the MFI data shown in FIG. 5.

FIG. 5 shows the flow cytometry results in MFI for the two donors, and FIG. 6 is a graphical representation of the same data shown in FIG. 5.

Example 3—Low Cytotoxic Effects after Liposome-Specific Targeting

Dendritic cell cytokine release and cytotoxic effects after Manα1-2Man-L interaction are studied. IL-6, IL-10, IL-12, and TNFα are measured after interaction with Manα1-2Man-L derivatives and control, in mouse and human DC cultures. The Manα1-2Man-L derivatives show low toxicity levels in both mouse and human DC cultures.

The results will show that the disclosed compounds, including Manα1-2Man-L, are a good tool for DC in vitro targeting. The liposomes are stable and slightly negatively charged, indicating that the binding is due to the specificity of the decoration and not because of a net charge attraction.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

All patents, patent applications and publications cited herein are hereby incorporated by reference in their entirety in order to more fully describe the state of the art as known to those skilled therein as of the date of the invention described herein.

We claim:
1. A compound having the structure of Formula (I),

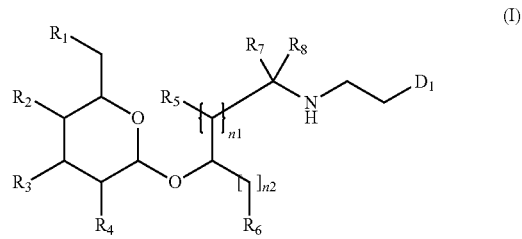

or a pharmaceutically acceptable salt or hydrate thereof, wherein
$R_1$, $R_2$, $R_3$, $R_4$, $R_5$, and $R_6$ are each independently H, OH, O-monosaccharide, NHAc, or Me;
$n_1$ and $n_2$ are each independently 0, 1, 2, 3, or 4, provided that the sum of $n_1$ and $n_2$ is 4;
$R_7$ and $R_8$ are each independently hydrogen, or $R_7$ and $R_8$ together form an oxo (=O); and
$D_1$ is a polymer selected from a group consisting of negative polymer, positive polymer, neutral polymer, linear or branched polymer, a lipid, hydrophobic carbon chain, nanoparticle organic molecule, nanoparticle inorganic molecule, drug, ribonucleic acids, peptide-nucleic acids (PNAs), and a mixture thereof.

2. The compound of claim 1, wherein the D1 is a peptide or a protein.

3. The compound of claim 1, wherein the $D_1$ is a polymer selected from the group consisting of a nylon, PVC, silicone, latex, polyvinyl butyral, polyacrylonitrile, polystyrene, polyethylene, polyethyleneglycol (PEG) or a PEG derivative, polyethyleneoxide (PEO), polyethyleneimine (PM), polyoxymethylene (POM), biodegradable polymers and a mixture thereof.

4. The compound of claim 3, wherein the PEG derivative is selected from the group consisting of PEG-DSPE, PEGCer (PEG-ceramide), PEGCerC14 (PEGCer containing a 14-carbon fatty acyl chain), PEGCerCzo (PEGCer containing a 20-carbon fatty acyl chain), PEG-COOH (carboxylated PEG-derivative), PEG-PE (poly(ethylene glycol)phosphatidylethanolamine), PEG-DPPE, PEG-DOPE, PEG-DMPE, fluorescent PEG-DSPE derivative, Succinyl-PEG, Carboxylic Acid-PEG, Maleimide-PEG, PDP-PEG, Amine-PEG, Biotin-PEG, Cyanur-PEG, Folate-PEG, PEG-Osu (poly(ethylene glycol) hydroxysuccinimide ester) and a mixture thereof.

5. The compound of claim 4, wherein the PEG derivative is PEG-DSPE, PEG-DPPE, PEG-DOPE, PEG-DMPE, PEG-ceramide, fluorescent PEG-DSPE derivative, Succinyl-PEG, Carboxylic Acid-PEG, Maleimide-PEG, PDP-PEG, Amine-PEG, Biotin-PEG, Cyanur-PEG, Folate-PEG, or a mixture thereof.

6. The compound of claim 5, wherein the PEG-ceramide is octanoyl-sphingosine, palmitoyl-sphingosine, or a mixture thereof.

7. The compound of claim 5, wherein the fluorescent PEG-DSPE derivative is carboxyfluorescein-PEG-DSPE.

8. The compound of any one of claims 1 and 3-7, having a structure selected from the group consisting of:

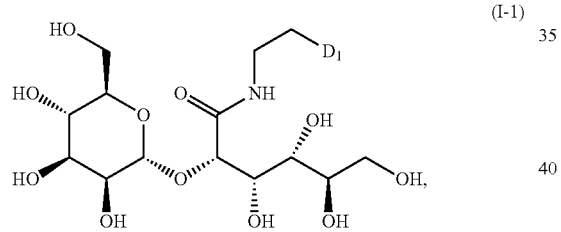
(I-1)

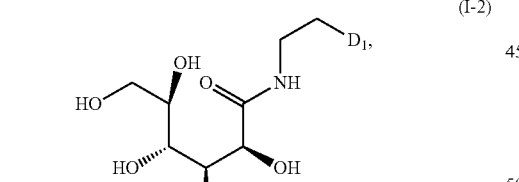
(I-2)

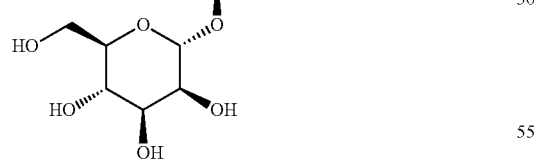
(I-13)

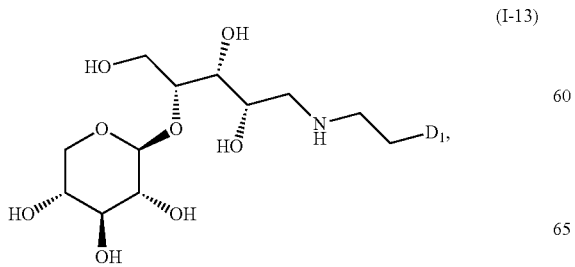

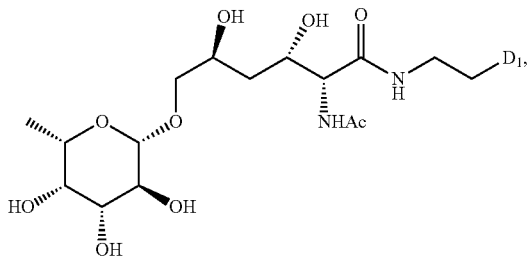
(I-14)

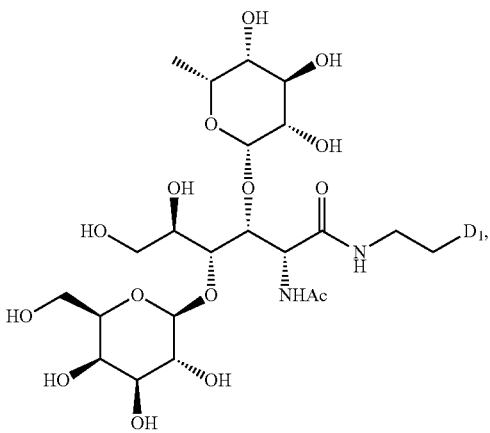
(I-15)

(I-16)

and

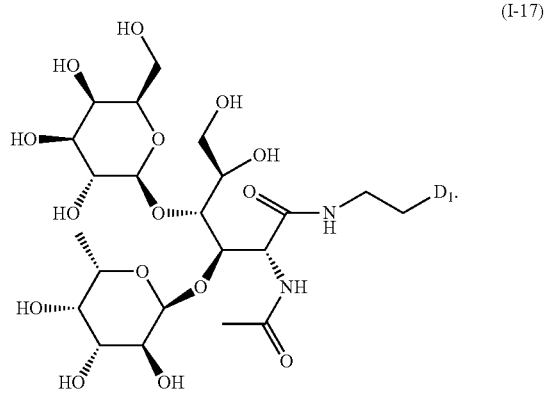
(I-17)

9. A compound having the structure of Formula (II),

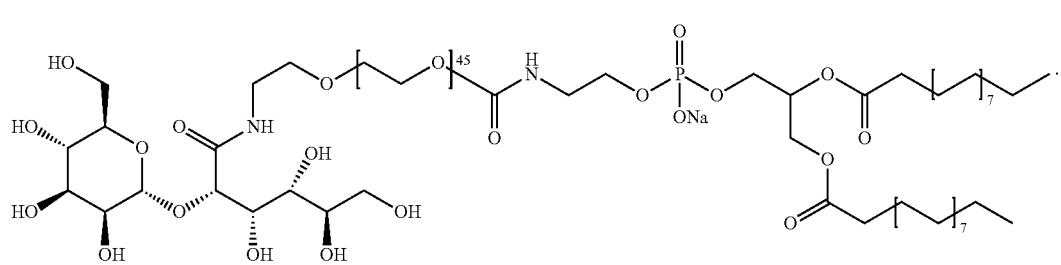

10. A pharmaceutical composition comprising the compound of any one of claims 1, 3, 4 and 9 and a pharmaceutically acceptable excipient.

11. The composition of claim 10, further comprising a nanocarrier.

12. The composition of claim 11, further comprising an active substance.

13. The composition of claim 12, wherein the active substance is an immunomodulator.

14. The composition of claim 13, wherein the immunomodulator is DNA, tRNA, siRNA, viral particle, protein, peptide, carbohydrate, glycoprotein, glycopeptides, proteoglycan, cell extract, hydrophilic drug, hydrophobic drug, B-cell antigen, T-cell antigen, antigen of a fungal, protozoan, parasitic organism, synthetic lipid, mineral, vegetal lipid, saponine, or mixtures thereof.

15. The composition of any one of claims 11-14, wherein the nanocarrier is formed by a phospholipid.

16. The composition of claim 15, wherein the nanocarrier is a liposome.

17. The composition of any one of claims 11-14, wherein the nanocarrier is a micelle.

18. The composition of any one of claims 11-14, wherein the nanocarrier is a synthetic nanocarrier.

19. The composition of any one of claims 11-14, wherein the nanocarrier is niosome, lipoprotein, carbon nanotube, nanocapsule, nanocrystal, silicon nanoparticle, calcium phosphate, ciclodextrin, metallic nanoparticle, dendrimer, protein-core nanoparticle, fullerene, or a mixture thereof.

20. A method of targeted delivery to an antigen-presenting cell, comprising contacting the antigen-presenting cell with at least one compound of any one of claims 1, 3-7, and 9.

21. A method of targeted delivery to an antigen-presenting cell, comprising contacting the antigen-presenting cell with the composition of claim 10.

22. The method of claim 20, wherein the antigen-presenting cell is a dendritic cell.

23. A method of treating a disease or condition susceptible to treatment by immunomodulation, the method comprising administering the composition of claim 10 to a subject, wherein the disease or condition is an infectious disease, cancer, an autoimmune disease, or transplant rejection.

24. The method of claim 21, wherein the antigen-presenting cell is a dendritic cell.

25. The method of claim 3, wherein the biodegradable polymer is one of polylactic acid (PLA) and polylactic co glycolic acid (PLGA).

* * * * *